(12) United States Patent
Sonoda et al.

(10) Patent No.: US 6,458,990 B1
(45) Date of Patent: Oct. 1, 2002

(54) NITROGEN-BASED HALOGENATING AGENTS AND PROCESS FOR PREPARING HALOGEN-CONTAINING COMPOUNDS

(75) Inventors: Hiroshi Sonoda, Fukuoka-ken (JP);
Kazunari Okada, Fukuoka-ken (JP);
Akira Takahashi, Fukuoka-ken (JP);
Kouki Fukumura, Fukuoka-ken (JP);
Hidetoshi Hayashi, Fukuoka-ken (JP);
Teruyuki Nagata, Fukuoka-ken (JP);
Yasuhiro Takano, Fukuoka-ken (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/987,613

(22) Filed: Nov. 15, 2001

Related U.S. Application Data

(62) Division of application No. 09/126,718, filed on Jul. 31, 1998, now Pat. No. 6,329,529.

(30) Foreign Application Priority Data

| Aug. 6, 1997 | (JP) | 9-212024 |
| Aug. 28, 1997 | (JP) | 9-232633 |
| Sep. 10, 1997 | (JP) | 9-245181 |
| Sep. 10, 1997 | (JP) | 9-245182 |
| Sep. 10, 1997 | (JP) | 9-245183 |
| Nov. 19, 1997 | (JP) | 9-318386 |
| Nov. 21, 1997 | (JP) | 9-321399 |
| Nov. 26, 1997 | (JP) | 9-324910 |
| Dec. 18, 1997 | (JP) | 9-349755 |
| Dec. 22, 1997 | (JP) | 9-353394 |
| Mar. 23, 1998 | (JP) | 10-073930 |
| Apr. 9, 1998 | (JP) | 10-097711 |
| Apr. 13, 1998 | (JP) | 10-101435 |
| Apr. 17, 1998 | (JP) | 10-107633 |
| Apr. 27, 1998 | (JP) | 10-116539 |

(51) Int. Cl.[7] .......................... C07C 17/16; C07C 21/18

(52) U.S. Cl. .................... 560/219; 562/849; 570/127; 570/129; 570/136

(58) Field of Search ................ 562/849, 861; 570/127, 129, 136; 560/219

(56) References Cited

U.S. PATENT DOCUMENTS 3,976,691 A   8/1976   Middleton

FOREIGN PATENT DOCUMENTS

| EP | 0249556 | 12/1987 |
| EP | 0751131 | 1/1997 |
| JP | 59-025375 | 2/1984 |
| JP | 04-308538 | 10/1992 |
| JP | 04-308547 | 10/1992 |
| JP | 08-012658 | 1/1996 |
| JP | 08-059604 | 3/1996 |

OTHER PUBLICATIONS

M.I. Povolotskii et al, "Synthesis and Dynamic Stereochemistry of C,C–bis(dialkylamino)phosphaalkenes", ZH. Obshch. Khim., vol. 60, No. 10, pp. 2238–2244, 1990, XP000926241.

L.N. Markovskii et al, "New Methods for the Synthesis of Phosphines", ZH. Obshch. Khim., vol. 52, No. 8, pp. 1925–1926, 1982, XP000926240.

F. Munyemana et al, "Synthesis of Alkyl Halides Under Neutral Conditions" Tetrahedron Letters, vol. 30, No. 23, pp. 3077–3080, 1989, XP002171329.

P. A. Messina et al, "Aminosulphur Trifluorides: Relative Thermal Stability" Journal of Fluorine Chemistry, Elsevier Sequoia, Lausanne, vol. 42, No. 1, pp. 137–143, 1989, XP002088199.

L.A. Carpino et al, "Tetramethylfluoroformamidinium Hexafluorophosphate: A Rapid–Acting Peptide Coupling Reagent for Solution and Solid Phase Peptide Synthesis", Journal Of The American Chemical Society, vol. 117, No. 19, pp. 5401–5402, 1995, XP002171330.

T. Kaneko et al, "New Chemistry of Mitomycin C", Tetrahedron Letters, vol. 26, No. 33, pp. 3923–3926, 1985, XP002171331.

*Primary Examiner*—Joseph K. McKane
*Assistant Examiner*—Kamal Saeed
(74) *Attorney, Agent, or Firm*—Burns, Doane, Swecker & Mathis, L.L.P.

(57) ABSTRACT

Disclosed are a fluorinating agent represented by the general formula (1):

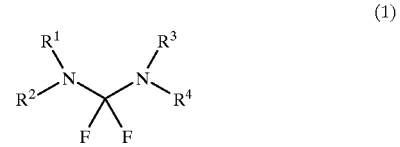

wherein $R^1$ to $R^4$ are a substituted or unsubstituted, saturated or unsaturated alkyl group or a substituted or unsubstituted aryl group, and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, for example:

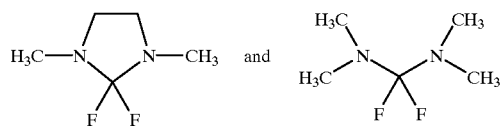

a preparation process of the fluorinating agent and a process for preparing fluorine compounds by reacting various compounds with the fluorinating agent. The invention has also disclosed that the fluorinating agent is very effective for fluorinating oxygen containing functional compounds.

6 Claims, 1 Drawing Sheet

NITROGEN-BASED HALOGENATING AGENTS AND PROCESS FOR PREPARING HALOGEN-CONTAINING COMPOUNDS

This application is a division of application Ser. No. 09/126,718 filed on Jul. 31, 1998 now U.S. Pat. No. 6,329,529.

BACKGROUND OF THE INVENTION

1. Field of the Invention

The present invention relates to a novel halogenating agent, preparation process and use of the agent.

2. Related Art of the Invention

Many processes have been conventionally known related to the halogenating reaction of organic compounds. Halogenating agents which can be generally used are hydrogen halogenide, halogen-phosphorus compounds, halogen-sulfur compounds and halogen simple substances. However, these substances have high corrosivity and toxicity, and many of them require specific equipment and technique for handling these agents. Consequently, in view of ease handling, safety and reactivity, development research on various halogenating agents has been continued still now. Particularly in the preparation of fluorine compounds, fluorinating agents are generally very dangerous. Thus, specific equipment and techniques having a further high level as compared with other halogenating reaction are required and also lead to higher load in economy.

Fluorinating agents which have been conventionally used for a fluorinating reaction are fluorine, hydrogen fluoride, and tetrafluorinated sulfur. However, these conventional fluorinating agents are difficult to handle due to toxicity, corrosivity and danger of explosion in the reaction step and require specific equipment and techniques. Further, poor selectivity of a fluorine bonding in the reaction is also a problem. On the other hand, development of new products utilizing fluorine compounds has been carried out in functional materials, physiologically active substances and other various fields. In recent years, various fluorinating agents have been developed to cope with these demands.

For example, as a representative agent which has been developed for a fluorinating agent of a hydroxyl group, carboxyl group and other oxygen containing functional groups, U.S. Pat. No. 3,976,691 has disclosed DAST (diethylaminosulfurtrifluoride). DAST has been introduced as an excellent fluorinating agent of oxygen in an alcoholic hydroxyl group or a carbonyl group. However, in the preparation of DAST, highly dangerous tetrafluorinated sulfur is reacted with dimethylaminotrimethylsilane at a low temperature of −78° C. to −60° C. Thus, a specific manufacturing facility is required. As to safety, explosion has been reported on the production and use of DAST [J. Fluorine Chem., 42 137 (1989)].

Further, WO 96/04297 has described that tetraalkyl-fluoroform-amidinium=salt is an excellent fluorinating agent of a carboxyl group. However, no description has been found on the fluorinating reaction of other functional groups. The application has described that halogen ions are included as a counter ion of tetraalkyl-fluoroformamidinium salt. However, in practice, $PF_6^-$ is an only one example shown as a counter ion. Therefore, the present inventors have prepared 1,3-dimethyl-2-fluoroimidazolinium=hexafluorophosphate in accordance with the process of WO 96/04297, and used for the replacement of individual hydroxyl group on benzoic acid, benzyl alcohol and n-octanol into fluorine. As a result, benzoyl fluoride has been formed from benzoic acid. However, formation of fluorine compounds could not be observed in the fluorinating reaction of benzyl alcohol and n-octanol. Japanese Laid-Open Patent HEI 4-308538 has disclosed a halogenating reaction of primary alcohol by using a haloiminium salt as a halogenating agent. Japanese Laid-Open Patent HEI 9-67299 has described a halogenation reaction of carboxylic acid. Both literatures have described that the counter ion of haloiminium salt includes a halogen ion. However, in practice, the counter ion is an example of Cl⁻ alone. Quite no description is found on a fluorinating agent in particular.

Further, DE 2627986 and Japanese Laid-Open Patent SHO 52-156810 have described use of bis-dialkylaminodifluoromethane as a reaction catalyst in the preparation of perfluoroalkoxypropionyl fluoride. However, no description has been found on a fluorinating agent. The preparation is carried out by reacting hexafluoropropene oxide with tetraalkylurea, and the source of fluorine is expensive and difficult to handle.

As a mentioned above, the fluorinating agent of an oxygen containing functional group has not yet satisfactorily developed for use in industry in view of preparation process, selectivity, yield and economy.

SUMMARY OF THE INVENTION

One object of the invention is to provide a halogenating agent of an organic compound, a fluorinating agent in particular, which eliminates the above problems of the prior art and can be prepared by a technically and economically improved process in industry and is excellent in reactivity and economy, to provide a preparation process of the halogenating agent, and to provide a preparation process of compounds obtained by halogenating, fluorinating in particular, various organic compounds with the agent.

As a result of an intensive investigation in order to solve the above objects, the present inventors have found that the compound represented by the formula (1):

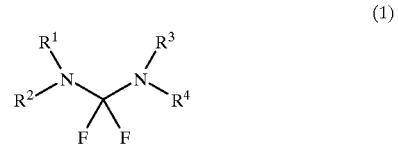

wherein $R^1$ to $R^4$ is a substituted or unsubstituted, saturated or unsaturated alkyl group or a substituted or unsubstituted aryl group and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, is a novel excellent fluorinating agent which is selective for a hydroxyl group, carboxyl group, formyl group, ketone group and other oxygen containing functional groups, and further found that application to the fluorinating reaction requires no specific equipment and technique and can be carried out in extreme safety and with ease.

Further, they have found that the compound represented by the formula (1) can be obtained by way of a halogen exchange reaction of the compound represented by the formula (14):

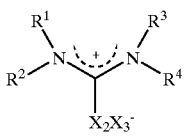
(14)

wherein $X_2$ and $X_3$ are chlorine or bromine atoms and can be the same or different; $R^1$ to $R^4$ is a substituted or unsubstituted, saturated or unsaturated alkyl group or a substituted or unsubstituted aryl group and can be the same or different ; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, and thus no specific equipment and technique are required and can be safely manufactured in industry.

They have also found that the fluorinating agent represented by the formula (1) can be recovered after fluorinating reaction in the form of urea and can be reused in economy for the raw material of the compound represented by the formula (14).

Further, they have also found that the compound represented by the formula (15):

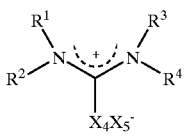
(15)

wherein $X_4$ and $X_5$ are halogen atoms and can be the same or different except that both Of $X_4$ and $X_5$ are fluorine atoms, chlorine atoms or bromine atoms; $R^1$ to $R^4$ is a substituted or unsubstituted, saturated or unsaturated alkyl group or a substituted or unsubstituted aryl group and can be the same or different; $R^1$ and $R^2$ or $R^3$ and $R^4$ can bond to form a ring including a nitrogen atom or a nitrogen atom and other hetero atoms, is an excellent, novel halogenating agent which is selective for a hydroxyl group, carboxyl group, formyl group and other oxygen containing functional groups, and further found that application to the halogenation reaction requires no specific equipment and technique and can be carried out in extreme safety with ease.

That is, the aspect of the invention will be illustrated from (1) to (45) below.

(1) A fluorinating agent represented by the formula (1):

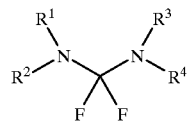
(1)

wherein $R^1$ to $R^4$ is a substituted or unsubstituted, saturated or unsaturated alkyl group, saturated or unsaturated aryl group, and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms.

(2) A fluorinating agent according to the above (1) wherein the fluorinating agent represented by the formula (1) is represented by the formula (2):

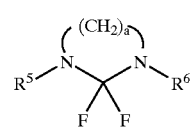
(2)

wherein a is an integer of 2 or 3, $R^5$ and $R^6$ are substituted or unsubstituted, saturated or unsaturated lower alkyl groups having 1 to 6 carbon atoms and can be the same or different.

(3) A fluorinating agent according to the above (2) wherein the fluorinating agent represented by the formula (2) is 2,2-difluoro-1,3-dimethylimidazolidine represented by the formula (3):

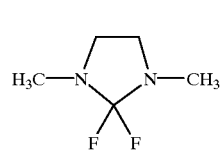
(3)

(4) A fluorinating agent according to the above (2) wherein the fluorinating agent represented by the formula (2) is 2,2-difluoro-1,3-di-n-butylimidazolidine represented by the formula (4):

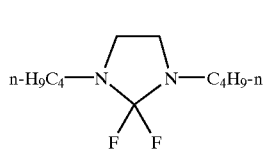
(4)

(5) A fluorinating agent according to the above (1) wherein the fluorinating agent represented by the formula (1) is represented by the formula(5):

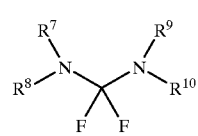
(5)

wherein $R^7$ to $R^{10}$ is a substituted or unsubstituted, saturated or unsaturated lower alkyl group having 1 to 6 carbon atoms, and can be the same or different; $R^7$ and $R^8$ or $R^9$ and $R^{10}$ can bond to form a ring including a nitrogen atom or a nitrogen atom and other hetero atoms; or $R^7$ and $R^9$ can bond to form a ring including a nitrogen atom or a nitrogen atom and other hetero atoms.

(6) A fluorinating agent according to the above (5) wherein the fluorinating agent represented by the formula (5) is bis-dimethylamino-difluoromethane represented by the formula (6):

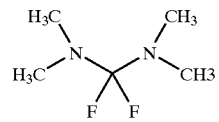
(6)

(7) A fluorinating agent according to the above (5) wherein the fluorinating agent represented by the formula (5) is bis-di-n-butylamino-difluoromethane represented by the formula (7):

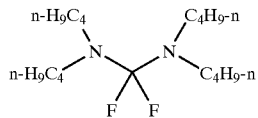
(7)

(8) A preparation process of a fluorine compound represented by the formula (8-1):

 (8-1)

wherein $R^{11}$ is a substituted or unsubstituted alkyl group and can include an unsaturated group therein, comprising reacting a compound having an alcoholic hydroxyl group and represented by the formula (8):

 (8)

wherein $R^{11}$ is the same as in the formula (8-1), with the above fluorinating agent represented by the formula (1).

(9) A preparation process of a fluorine compound represented by the formula (9-1):

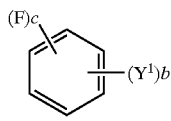
(9-1)

wherein $Y^1$ is an electrophilic substituent, b is an integer of 1 to 5, c is an integer of 1 to 5, and b+c≦6, comprising reacting a compound of phenol species or thiophenol species represented by the formula (9):

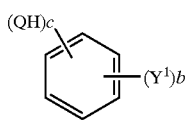
(9)

wherein Q is an oxygen or a sulfur atom, and $Y^1$, b and c are the same as in the formula (9-1), with the above fluorinating agent represented by the formula (1).

(10) A preparation process of a fluorine compound represented by the formula (10-1):

 (10-1)

wherein $R^{12}$ is a substituted or unsubstituted, saturated or unsaturated alkyl group, or a substituted or unsubstituted aryl group, comprising reacting an aldehyde compound represented by the formula (10):

 (10)

wherein $R^{12}$ is the same as in the formula (10-1), with the above fluorinating agent represented by the formula (1).

(11) A preparation process of a fluorine compound represented by the formula (11-1):

(11-1)

wherein $R^{13}$ and $R^{14}$ are a substituted or unsubstituted alkyl group or a substituted or unsubstituted aryl group and can be the same or different; the alkyl group can include unsaturated group, and $R^{13}$ and $R^{14}$ can bond to form a ring, comprising reacting a ketone compound represented by the formula (11):

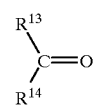
(11 wherein $R^{13}$ and $R^{14}$ are the same as in the formula (11-1), with the above fluorinating agent represented by the formula (1).

(12) A preparation process of an acid fluoride represented by the formula (12-1):

 (12-1)

wherein $R^{15}$ is a substituted or unsubstituted, saturated or unsaturated alkyl group or a substituted or unsubstituted aryl group, comprising reacting a carboxyl compound represented by the formula (12):

 (12)

wherein $R^{15}$ is the same as in the formula (12-1), with the above fluorinating agent represented by the formula (1).

(13) A preparation process of a fluorine compound represented by the formula (13-1):

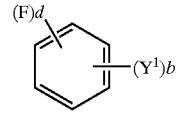
(13-1 wherein $Y^1$ is an electrophilic substituent, b and d are integers of 1 to 5, and b+d >6, comprising reacting an aromatic compound comprised of a halogen atom except fluorine and represented by the formula (13):

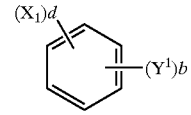
(13 wherein $X_1$ is a halogen atom except fluorine, and $Y^1$, b and d are the same as in the formula (13-1), comprising reacting with the above fluorinating agent represented by the formula (1).

(14) A preparation process of a fluorine containing olefinic compound represented by the formula (25)

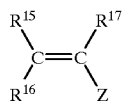

wherein $R^{15}$ to $R^{17}$ are a hydrogen atom or a lower alkyl group having 1 to 3 carbon atoms and can be the same or different; and Z is —(Y)n—CHF$_2$—(Y)n—CH$_2$F or —CO—O—(Y)n—CH$_2$F, wherein Y is —CH$_2$— and n is 0 or an integer of 1 to 5, comprises reacting a fluorinating agent represented by the formula (1) with olefinic compounds represented by the formula (24)

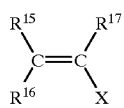

wherein $R^{15}$ to $R^{17}$ are a hydrogen atom or a lower alkyl group having 1 to 3 carbon atoms and can be the same or different; and X is —(Y)n—CHO, —(Y)n—CH$_2$OH, or —CO—O—(Y)n—CH$_2$OH, wherein Y is —CH$_2$— and n is 0 or an integer of 1 to 5.

(15) A process according to one of the above 8 to 14 wherein the fluorinating agent is represented by the formula (2).

(16) A compound represented by the formula (2):

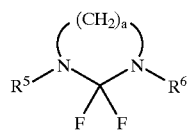

wherein a is an integer of 2 or 3, $R^1$ and $R^6$ are a substituted or unsubstituted, saturated or unsaturated lower alkyl group having 1 to 6 carbon atoms and can be the same or different.

(17) A compound wherein the formula (2) is 2,2-difluoro-1,3-dimethylimidazolidine represented by the formula (3):

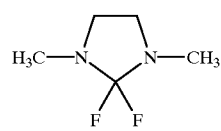

(18) A compound wherein the formula (2) is 2,2-difluoro-1,3-di-n-butylimidazolidine represented by the formula (4):

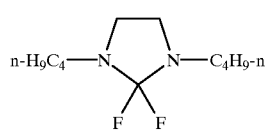

(19) A compound wherein the formula (5) is bis-di-n-butylamino-difluoromethane represented by the formula (7):

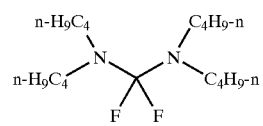

(20) A preparation process of a fluorinating agent represented by the formula (1) in the above (1) comprising carrying out a halogen exchange reaction of a compound represented by the formula (14):

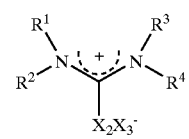

wherein $X_2$ and $X_3$ are a chlorine or a bromine atom, $R^1$ to $R^4$ are substituted or unsubstituted, saturated or unsaturated alkyl group, substituted or unsubstituted aryl group, and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, with an alkali metal salt of a fluorine atom in an inert solvent.

(21) A preparation process of a fluorinating agent of the above (1) comprising reacting a compound represented by the formula (14) with a half equivalent of sodium fluoride, separating by filtration, and successively reacting with potassium fluoride.

(22) A halogenating agent represented by the formula (15):

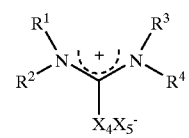

wherein $X_4$ and $X_5$ are a halogen atom and can be the same or different except that both $X_4$ and $X_5$ are not fluorine atoms, chlorine atoms or bromine atoms; $R^1$ to $R^4$ are a substituted or unsubstituted, saturated or unsaturated alkyl group or a substituted or unsubstituted aryl group, and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms.

(23) A halogenating agent according to the above (22) wherein the halogenating agent represented by the formula (15) is represented by the formula (16):

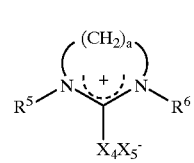

wherein $X_4$ and $X_5$ are a halogen atom and can be the same or different except that both $X_4$ and $X_5$ are not fluorine atoms, chlorine atoms or bromine atoms; a is an integer of 2 or 3, $R^1$ and $R^6$ are a substituted or unsubstituted, saturated or unsaturated lower alkyl group having 1 to 6 carbon atoms and can be the same or different.

(24) A halogenating agent according to the above (23) wherein the halogenating agent represented by the formula (16) is 2-halo-1,3-dimethylimidazolinium=halide represented by the formula (17):

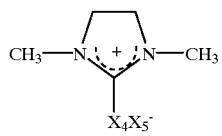

(17)

wherein $X_4$ and $X_5$ are a halogen atom and can be the same or different except that both $X_4$ and $X_5$ are not fluorine atoms, chlorine atoms or bromine atoms.

(25) A halogenating agent according to the above (23) wherein the halogenating agent represented by the formula (16) is 2-fluoro-1,3-dimethylimidazolinium=chloride represented by the formula (18):

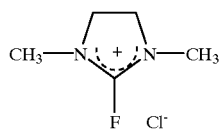

(18)

(26) A halogenating agent according to the above (23) wherein the halogenating agent represented by the formula (16) is 2-fluoro-1,3-dimethylimidazolinium=bromide represented by the formula (19):

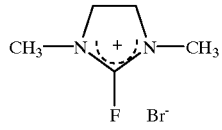

(19)

(27) A halogenating agent according to the above (23) wherein the halogenating agent represented by the formula (16) is 2-fluoro-1,3-dimethylimidazolinium=iodide represented by the formula (20):

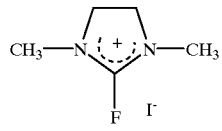

(20)

(28) A halogenating agent according to the above (23) wherein the halogenating agent represented by the formula (16) is 2-chloro-1,3-dimethylimidazolinium=bromide represented by the formula (21):

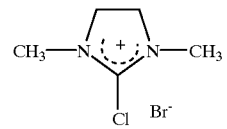

(21)

(29) A halogenating agent according to the above (23) wherein the halogenating agent represented by the formula (16) is 2-chloro-1,3-dimethylimidazolinium=iodide represented by the formula (22):

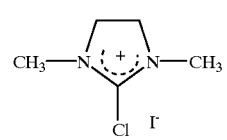

(22)

(30) A halogenating agent according to the above (23) wherein the halogenating agent represented by the formula (16) is 2-iodo-1,3-dimethylimidazolinium=iodide represented by the formula (23):

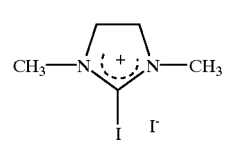

(23)

(31) A preparation process of a halogenating agent represented by the above formula (15) according to the above (21) comprising carrying out a halogen exchange reaction of a compound represented by the formula (14):

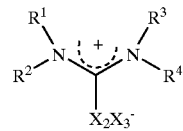

(14)

wherein $X_2$ and $X_3$ are a chlorine or bromine atom and $R^1$ to $R^4$ are the same as above, with an alkali metal salt of a fluorine atom, chlorine atom, bromine atom or iodine atom or a mixture thereof in an inert solvent.

(32) A preparation process of a halogen compound represented by the formula (8-2):

$$R^{11}\text{—}X_5 \tag{8-2}$$

wherein $R_{11}$ is a substituted or unsubstituted alkyl group and can include an unsaturated group therein and $X_5$ is a halogen atom, comprising reacting an alcoholic hydroxyl compound represented by the formula (8):

$$R^{11}\text{—OH} \tag{8}$$

wherein $R^{11}$ is the same as in the formula (8-2), with the above halogenating agent represented by the formula (15):

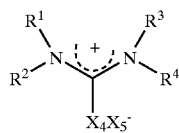
(15)

wherein $X_4$, $X_5$, and $R^1$ to $R^4$ are the same as above.

(33) A preparation process of an acid halogenide species represented by the formula (12-2):

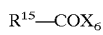  (12-2)

wherein $R^{15}$ is a substituted or unsubstituted, saturated or unsaturated alkyl group or substituted or unsubstituted aryl group and $X_6$ is a halogen atom represented by $X_4$ or $X_5$ in the formula (15), comprising reacting a carboxylic acid compound represented by the formula (12):

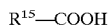  (12)

wherein $R^{15}$ is the same as in the formula (12-2), with a halogenating agent represented by the formula (15):

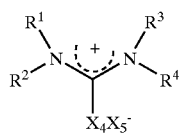
(15)

wherein $X_4$, $X_5$ and $R^1$ to $R^4$ are the same as above.

(34) A preparation process of a fluorine compound represented by the formula (10-2):

  (10-2)

wherein $R^{12}$ is a substituted or unsubstituted, saturated or unsaturated alkyl group, or a substituted or unsubstituted aryl group, and $X_7$ is a halogen atom represented by $X_4$ or $X_5$ in the formula (15) and two $X^7$ can be the same or different, comprising reacting an aldehyde compound represented by the formula (10):

  (10)

wherein $R^{12}$ is the same as in the formula (10-2), with a halogenating agent represented by the formula (15):

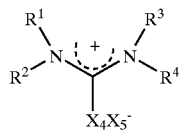
(15)

wherein $X_4$, $X_5$ and $R^1$ to $R^4$ are the same as above.

(35) A preparation process of a halogen compound according to one of the above 32 to 34 wherein the halogenating agent is represented by the formula (17).

(36) A compound represented by the formula (15):

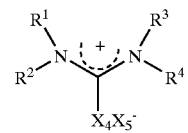
(15)

wherein $X_4$ and $X_5$ are a halogen atom and can be the same or different except that both $X_4$ and $X_5$ are not fluorine atoms, chlorine atoms or bromine atoms; $R^1$ to $R^4$ are a substituted or unsubstituted, saturated or unsaturated alkyl group or a substituted or unsubstituted aryl group and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms.

(37) A compound represented by the formula (16):

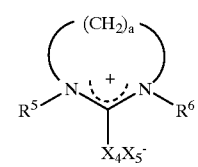
(16)

wherein $X_4$ and $X_5$ are same or different halogen atom except that both $X_4$ and $X_5$ are fluorine atom, chlorine atom or bromine atom, a is an integer of 2 or 3, $R^5$ and $R^6$ are a substituted or unsubstituted, saturated or unsaturated lower alkyl group having 1 to 6 carbon atoms and can be the same or different.

(38) A halogenating agent according to the above (22) wherein the halogenating agent is 2-halo-1,3-dimethylimidazolinium=halide represented by the formula (17):

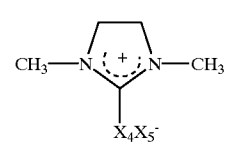
(17)

wherein $X_4$, $X_5$ are the same as above.

(39) A compound, 2-fluoro-1,3-dimethylimidazolinium= chloride represented by the formula (18):

(18)

$$CH_3-N\overset{+}{\underset{F}{\diagdown \diagup}}N-CH_3 \quad Cl^-$$

(40) A compound, 2-fluoro-1,3-dimethylimidazolinium= bromide represented by the formula (19):

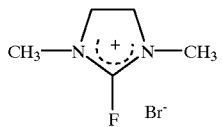

(19)

(41) A compound, 2-fluoro-1,3-dimethylimidazolinium= iodide represented by the formula (20):

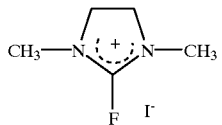

(20)

(42) A compound, 2-chloro-1,3-dimethylimidazolinium= bromide represented by the formula (21):

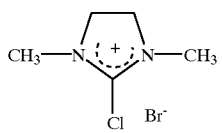

(21)

(43) A compound, 2-chloro-1,3-dimethylimidazolinium iodide represented by the formula (22):

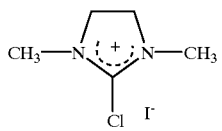

(22)

(44) A compound, 2-iodo-1,3-dimethylimidazolinium iodide represented by the formula (23):

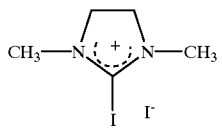

(23)

(45) A preparation process of a halogenating agent represented by the formula (15):

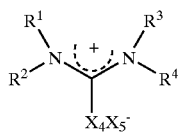

(15)

wherein $R^1$ to $R^4$, $X_4$ and $X_5$ are the same as above, comprising carrying out a halogen exchange reaction of a compound represented by the formula (1):

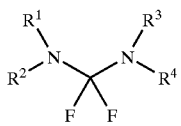

(1)

wherein $R^1$ to $R^4$ are the same as above, with an alkali metal salt of chlorine a chlorine, bromine or iodine atom in the presence of an inert solvent.

The halogenating agent of the invention, fluorinating agent in particular, is a fluorinating agent for a hydroxyl group, carboxyl group and other oxygen containing functional groups of a compound, can be handled with safety and ease, and has high selectivity. Preparation of the fluorinating agent of the invention requires no specific equipment and technique and can be carried out with economy. Further, a halogenating agent obtained by substituting other halogen atom for the fluorine atom can also be applied to the preparation of compounds having halogen other than fluorine.

The halogenating agent of the invention, fluorinating agent in particular, has eliminated problems of conventional techniques for the preparation of the agent itself in industry and exhibits excellent effects as a halogenating agent, fluorinating agent in particular, for organic compounds particularly having an oxygen containing functional group.

DETAILED DESCRIPTION OF THE INVENTION

Figure 1:
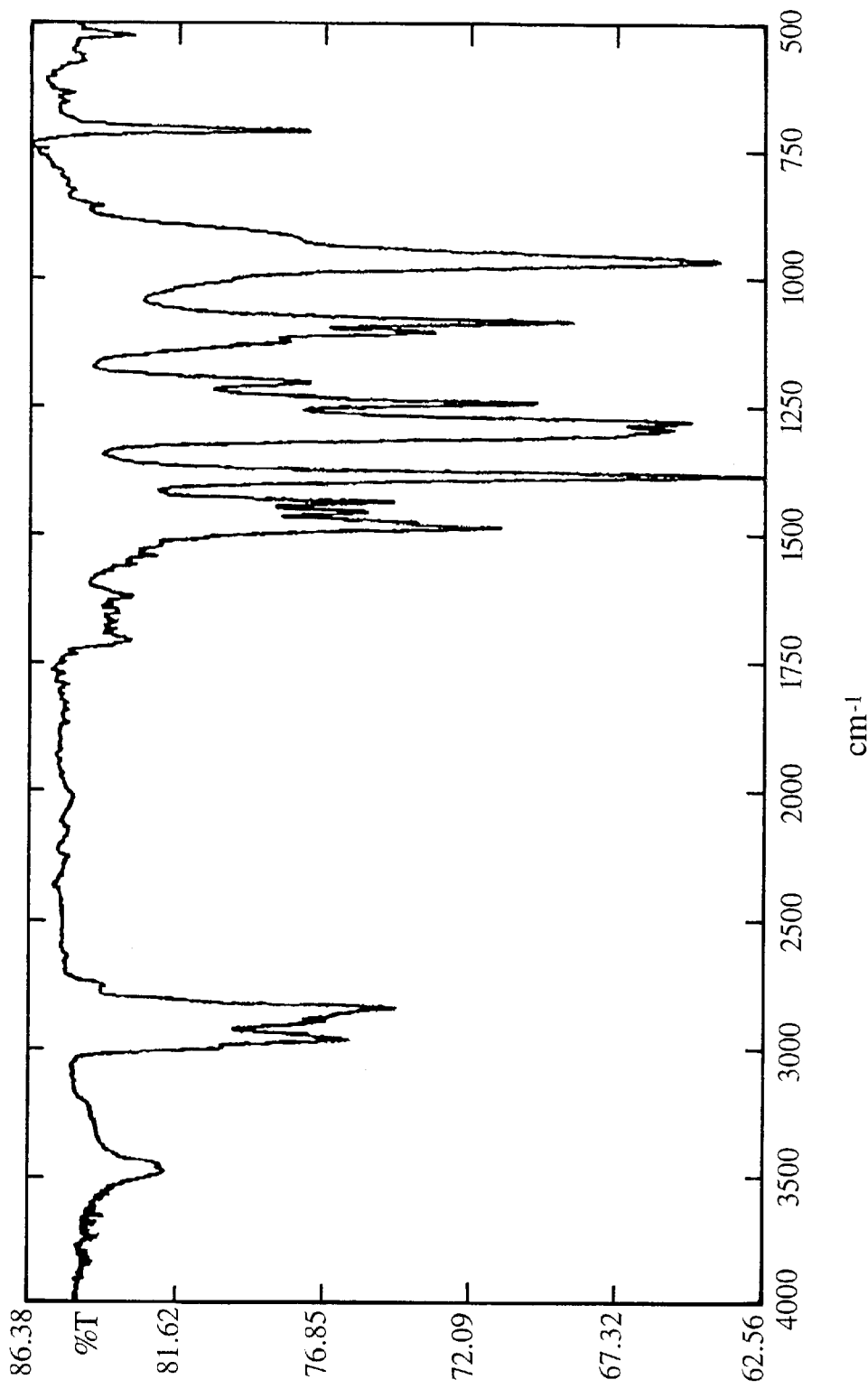
FIG. 1 is an IR spectrum of 2,2-difluoro-1,3-dimethylimidazolidine prepared in Example 1.

The fluorinating agent will be described.

The fluorinating agent of the invention is a compound represented by the above formula (1):

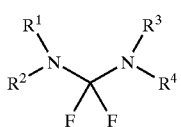

(1)

wherein $R^1$ to $R^4$ are the same as above.

In the formula (1), $R^1$ to $R^4$ are individually a substituted or unsubstituted, saturated or unsaturated alkyl group, or a substituted or unsubstituted aryl group, and can be the same or different; $R^1$ and $R^2$ or $R^3$ and $R^4$ can bond to form a ring including a nitrogen atom or a nitrogen atom and other hetero atoms, or $R^1$ and $R^3$ can bond to form a ring including a nitrogen atom or a nitrogen atom and other hetero atoms. $R^1$ to $R^4$ are preferably an alkyl or aryl group having 1 to 6 carbon atoms. The alkyl group can be straight or branched, and includes a methyl, ethyl, n-propyl, allyl, isopropyl, n-butyl, butenyl and n-hexyl group. The aryl group includes a phenyl group. $R^1$ to $R^4$ can be the same or different.

Further, $R^1$ and $R^2$ or $R^3$ and $R^4$ can individually bond to form a heterocyclic ring which includes a nitrogen atom and has 3 to 5 carbon atoms, for example, a pyrrolidine ring and piperidine ring.

Moreover, $R^1$ and $R^3$ can bond to form a five membered ring or six membered ring which includes two nitrogen atoms in the ring, for example, an imidazolidine ring, imidazolidinone ring, pyrimidine ring and pyrimidinone ring.

Practical examples of the fluorinating agent which is represented by the formula (1) and preferably used in the invention include below described compounds. However, the scope of the invention is not limited by the compounds shown below.

(1) Examples of the compound

Bis-dimethylamino-difluoromethane, bis-diethylamino-difluoromethane, bis-di-n-propylamino-difluoromethane, bis-di-isopropylamino-difluoromethane, bis-di-allylamino-difluoromethane, bis-di-n-butylamino-difluoromethane, bis-di-n-hexylamino-difluoromethane, bis-(1-pyrrolidyl)-difluoromethane, bis(1-piperidyl)-difluoromethane, 2,2-difluoro-1,3-dimethyl-imidazolidine, 2,2-difluoro-1,3-diethyl-imidazolidine, 2,2-difluoro-1.3-di-n-propyl-imidazolidine, 2,2-difluoro-1,3-diisopropyl-imidazolidine, 2,2-difluoro-1,3-diallyl-imidazolidine, 2,2-difluoro-1,3-di-n-butyl-imidazolidine, bis(N-methyl-N-phenyl) difluoromethane, 2,2-difluoro-1,3-dimethyl-imidazolidine-4,5-dione, 2,2-difluoro-1,3-di-n-butyl-imidazolidine-4,5-dione, and 2,2-difluoro-1,3-dimethyl-pyrimidine.

Particularly preferred agents are 2,2-difluoro-1,3-dimethyl-imidazolidine represented by the formula (3), 2,2-difluoro-1,3-di-n-butyl-dimidazolidine represented by the formula (4), bis-dimethylamino-difluoromethane represented by the formula (6), and bis-di-n-butylamino-difluoromethane represented by the formula (7).

The fluorinating agent represented by the formula (1) in the invention can be prepared by the following process.

That is, a compound represented by the formula (14):

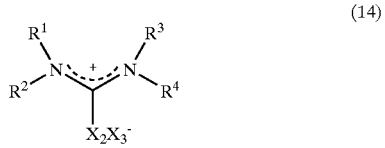

(14)

wherein $X_2$ and $X_3$ are a chlorine or a bromine atom and can be the same or different; $R^1$ to $R^4$ are substituted or unsubstituted, saturated or unsaturated alkyl group, or a substituted or unsubstituted aryl group, and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, is subjected to a halogen exchange reaction with an alkali metal salt of fluorine in an inert solvent. The fluorinating agent can be safely obtained with ease.

Alkali metal salts of fluoride, which can be used are cesium fluoride, rubidium fluoride, potassium fluoride and sodium fluoride. Preferred alkali metal salts of fluoride is a spray-dried potassium fluoride for use in a fluorinating reaction. The grade is advantageous in view of economy and reaction efficiency.

$X_2$ and $X_3$ in the formula (14) are usually chlorine atoms. However, compounds having bromine atoms as $X_2$ and $X_3$ can also be used.

Practical compounds include tetraalkylchloroformamidinium=chloride, 2-chloro-1,3-dialkylamidinium=chloride, tetraalkylbromoformamidinium=bromide, and 2-bromo-1,3-dialkylamidinium=bromide.

The compound represented by the formula (14) used as raw material for preparing the compound represented by the formula (1) includes, for example, tetraalkylurea, tetraalkylthiourea, N,N'-dialkylimidazolidinone or N,N'-dialkylimidazolithione with a halogenating agent such as phosgene, thionyl chloride, thionyl bromide, phosphorus trichloride or phosphorus tribromide.

For example, 2-chloro-1,3-dimethylimidazolinium=chloride can be prepared with ease by way of the process described in Japanese Laid-Open Patent SHO 59-25375. Practically, a solution of oxalyl chloride in carbon tetrachloride is dropwise added to 1,3-dimethylimidazolidinone and reacted at room temperature to 60 for several to several dozens hours.

In the preparation of the fluorinating agent represented by the formula (1) in the invention, the amount of alkali metal salt of fluorine for use in the halogen exchange reaction is preferably two equivalents or more, more preferably 2 to 5 equivalents for the amount of tetraalkyl-haloformamidinium=halide. The amount less than 2 equivalents leaves unexchanged halide. On the other hand, the amount exceeding 5 equivalents brings no remarkable improvement on the reaction yield.

No particular restriction is imposed upon the solvent of halogen exchange reaction so long as the solvent does not react with tetraalkyl-haloformamidinium=halide and generated compounds. Preferred solvents include acetonitrile, dimethylformamide, 1,3-dimethyl-2-imidazolidinone, dichloromethane and ethylene dichloride.

No particular limitation is put upon the amount of solvent in the reaction. However, the amount is preferably 1 to 10 times by weight for the reacting substance in view of reaction efficiency and ease of operation. The reaction temperature is in the range of −20 to 150° C., preferably 0 to 100° C. in view of reaction velocity and stability of formed product.

The halogen exchange reaction in the preparation of the fluorinating agent of the invention can also be carried out in the presence of a phase transfer catalyst such as quaternary ammonium salt or quaternary alkylphosphonium salt. The reaction mixture of the halogen exchange reaction can be used as is for the next fluorinating reaction, or can also be used for the next halogenation reaction after filtering the organic salt and distilling off the reaction solvent. The reaction product can also be isolated by distillation and used.

The fluorinating reaction using the fluorinating agent of the invention can be carried out with extreme ease by using conventional reaction equipment. For example, fluorinating reaction of carboxylic acid can be carried out by simply adding carboxylic acid to the reaction mixture of the halogen exchange reaction and reacting at room temperature for several hours. The corresponding fluoride of the carboxylic acid compound can be thus obtained in high yield.

Fluorinating reaction of alcohol species can also be carried out by directly charging the alcohol compound to the reaction mass of the halogen exchange reaction and reacting for several hours. The corresponding fluoride can be obtained in high yield.

The fluorinating reaction using the fluorinating agent of the invention will hereinafter be illustrated in detail.

(1) Conventionally, direct conversion of an alcoholic hydroxyl group into a fluorine group is a general-purpose, attractive process in the synthetic method of monofluoro compounds.

Representative fluorinating agents which are effective for the conversion reaction include hydrogen fluoride which is an acid agent, pyridine-(HF)n, fluoroalkylamine (Yarovenko's reagent), diethylamine-hexafluoropropane adduct (hereinafter referred to simply as PPDA), $SF_4$ (a four valent sulfur compound), trifluorodiethylaminosulfur (hereinafter referred to simply as DAST) and $PhPF_4$ (a five valent phosphorus compound).

As mentioned above, hydrogen fluoride has disadvantage upon difficulty to handle because of toxicity, corrosivity and danger to explosion in the reaction step and requirement for specific equipment and technique. Pyridine-(HP)n has fluorination ability higher than hydrogen fluoride itself. However, the ability is not so high as compared with other fluorination agents.

The Yarovenko's reagent: fluoroalkylamine is a fluorinating agent obtained by addition of diethylamine to chlorotrifluoroethene. The agent can fluorinate many kinds of primary and secondary alcohols under mild conditions in a solvent. However, the agent itself has low stability (can preserve for several days in a sealed, cold, dark place)[J. Gen Che. USSR 19, 2125 (1959)].

PPDA is more frequently used because the agent is more stable, can be handled with more ease, and has similar reactivity.

Recently, N,N-diisopropyl-2-fluoroenamine has been reported as a new type fluorinating agent of fluoroamine base [Tetrahedron Lett., 30, 3077 (1989)].

These reagents are useful for the fluorinating agents of an alcoholic hydroxyl group. However, application to an industrial scale is difficult to practice in view of complex procedures in synthesis and economy.

Additionally, DAST has similar problems as above also in the substitution of an alcoholic hydroxyl group for a fluorine group.

The fluorinating agent of the invention can be handled with safety and ease and provide a fluorinated material in high selectivity.

The problems of conventional fluorinating agents in the fluorinating reaction of an alcoholic hydroxyl group can be eliminated by using the fluorinating agent of the invention.

Preparation process of a fluorine compound from an alcoholic hydroxyl compound, by use of a fluorinating agent of the invention, is as follows.

That is, an alcoholic hydroxyl compound represented by the formula (8):

$$R^{11}—OH \quad (8)$$

wherein $R^{11}$ is the same as above, is reacted with the fluorinating agent of the invention to prepare a fluorine compound represented by the formula (8-1):

$$R^{11}—F \quad (8\text{-}1)$$

wherein $R^{11}$ is the same as above.

Representative alcohol compounds which have a hydroxyl group to be fluorinated include, for example, methyl alcohol, ethyl, n-propyl, n-butyl, isobutyl, 2-methyl-1-butyl, n-amyl, neoamyl, isoamyl, n-hexyl, 2-methyl-1-pentyl, 2-ethyl-1-butyl, n-heptyl, n-octyl, 2-ethlhexyl, n-nonyl, 3,5,5-trimethyl-1-hexyl, n-decyl, n-undecyl, n-dodecyl, allyl, methallyl, crotyl, benzyl, phenetyl, cinnamyl, propargyl, 2-hydroxyethylacrylate, 2-hydroxyethylmethacrylate and other primary alcohols; isopropyl, sec-butyl, sec-amyl, sec-isoamyl, 1-ethyl-1-propyl, 4-methyl-2-pentyl, 1-methylhexyl, 1-ethylpentyl, 1-methylheptyl, cyclohexyl, 2-methylcyclohexyl, 3-methylcyclohexyl, 4-methylcyclohexyl, sec-phenetyl and other secondary alcohols; and tert-butyl alcohol, tert-amyl, 1-methylcyclohexyl, α-terpine and other tertiary alcohols. However, alcohol species is not limited to these compounds.

These alcohols represented by the formula (8) can individually provide corresponding alkyl fluoride represented by the formula (8-1).

The amount of the fluorinating agent is usually 1 equivalent or more for the alcoholic hydroxyl group. Hydrogen fluoride generated in the reaction can be caught by using bases such as tertiary amine.

No particular restriction is imposed upon the solvent of reaction so long as the solvent does not react with the fluorinating agent and fluorine compounds formed by fluorination alcohol. Preferred solvents are acetonitrile, dichloromethane, ethylene dichloride, dimethylformamide and 1,3-dimethyl-2-imidazolidinone.

The reaction temperature depends upon the solvent and reactivity of the alcoholic hydroxyl group and is usually in the range of −40 to 100° C., preferably −20 to 80° C. in view of reaction velocity and stabilityof tetraalkyl-fluoroformaminium-fluoride.

When a formed fluorine compound has a low boiling point or a structure liable to release hydrogen fluoride, the reaction temperature is required to be as low as possible.

The fluoro compound formed by the reaction can be isolated with ease from the reaction mixture by distillation or other means.

(2) Conversion of a phenolic hydroxyl group to a fluoro group is considered to be possible by application of conventionally known fluorinating agents such as hydrogen fluoride, pyridine-(HF)n, fluoroalkylamine (Yarovenko's reagent), PPDA, $SF_4$ (four valent sulfur compound), DAST, and $PhPF_4$ (five valent phosphorus compound). However, no example has been found at all on the application of these fluorinating agents to such conversion reaction. Even though, these fluorinating agents can be applied, the same problems as above will occur in the reaction.

The fluorinating agent of the invention can also be favorably used for the fluorinating reaction of a phenolic hydroxyl group.

Fluorinating reaction of thiophenol can also be carried out. However, the reaction is liable to accompany formation of disulfide compounds as a by-product.

The fluorinating reaction of phenolic hydroxyl group can position-selectively introduce a fluorine atom into the aromatic ring to prepare an aromatic fluorine compound. The reaction process is as follows.

That is, a phenol compound or thiophenol compound represented by the formula (9):

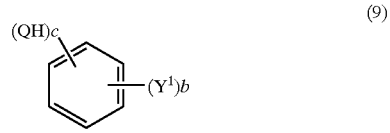

wherein $Q$, $Y^1$, b and c are the same as above, is reacted with the fluorinating agent of the invention to prepare a fluorinated phenol compound represented by the formula (9-1):

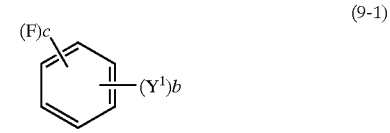

wherein $Y^1$, b and c are the same as in the formula (9).

The phenolic compound which can be fluorinated has on the aromatic ring thereof one or more electrophilic substituents such as $NO_2$, —CN, —$CF_3$, —CHO, —COOH, and —CO—. Preferred phenolic compounds include, for example, o-nitrophenol, p-nitrophenol, o-cyanophenol, p-cyanophenol, p-hydroxybenzaldehyde, o-hydroxybenzaldehyde, p-hydroxytrifluoromethylbenzene, o-hydroxy-trifluoromethylbenzene, p-hydroxy-benzoicmethyl ester, o-hydroxy-benzoicmethyl ester, 4,4'-dihydroxy-benzophenone, p-hydroxy-benzoic acid, o-nitrothiophenol and p-nitrothiophenol. However, phenolic and thiophenolic compounds are not limited to these compounds.

These phenol or thiophenol compounds represented by the formula (9) provide corresponding fluorine compounds represented by the formula (9-1).

The amount of fluorinating agent is usually 1 equivalent or more for a phenolic hydroxyl group. Hydrogen fluoride generated in the reaction can be caught with a base such as tertiary amine.

No particular restriction is imposed upon the solvent of the reaction so long as the solvent does not react with the fluorinating agent and fluorine compounds generated by fluorination of phenols. Preferred solvents are acetonitrile, dichloromethane, ethylene dichloride, dimethylformamide and 1,3-dimethyl-2-imidazolidinone.

The reaction temperature depends upon the solvent and reactivity of phenolic hydroxyl group, and usually in the range of –0 to 150° C., preferably 20 to 110° C. in view of reaction velocity and stability of tetraalkyl-fluoroformamidium=fluoride.

The fluorine compound formed by the reaction can be isolated with ease from the reaction mixture by means of distillation.

(3) Direct conversion of formyl oxygen to a fluorine group is also a useful method for preparing a fluorine compound.

As to a direct fluorination of a formyl group or a carbonyl group of ketone, $SF_4$ and DAST have been known in the above fluorinating agents. However, these fluorinating agents are unsatisfactory because of a severe restriction due to the above mentioned reason.

The fluorinating agent of the invention can effectively achieve fluorination of ketone groups. The process thereof is as follows.

That is, an aldehyde compound represented by the formula (10):

$$R^{12}\text{—CHO} \qquad (10)$$

wherein $R^{12}$ is a substituted or unsubstituted, saturated or unsaturated alkyl group or a substituted or unsubstituted aryl group, is reacted with a fluorinating agent of the invention to prepare the fluorine compound represented by the formula (10-1):

$$R^{12}\text{—CHF}_2 \qquad (10\text{-}1)$$

wherein $R^{12}$ is the same as in the formula (10).

Thus, the direct fluorination of formyl oxygen can be effectively achieved by using the fluorinating agent of the invention.

Exemplary compounds which have a fluorinatable formyl group include, for example, formaldehyde, acetaldehyde, acrolein, methacrolein, propionaldehyde, butyraldehyde, isobutylaldehyde, valeraldehyde, isovaleraldehyde, hexaldehyde, heptaldehyde, octylaldehyde, nonylaldehyde, decylaldehyde and other aliphatic aldehydes; cyclohexanecarboxyaldehyde and other alicyclic aldehydes; benzaldehyde, p-nitrobenzaldehyde, anisaldehyde, phthalaldehyde, 1-naphthoaldehyde and other aromatic aldehydes; and nicotinaldehyde, furfural and other heterocyclic aldehydes. However, aldehyde is not limited to these compounds.

Fluorine compounds corresponding to these aldehyde compounds and having the formula (10-1) can be obtained.

The amount of the fluorinating agent is preferably 1 equivalent or more for a formyl group.

No particular restriction is imposed upon the solvent of the reaction so long as the solvent does not react with the fluorinating agent, formyl compound and reaction product. Preferred solvents are acetonitrile, dichloromethane, chloroform, ethylene dichloride, 1,2-dimethoxyethane, diethylene glycol dimethyl ether, N-methylpyrrolidinone, dimethylformamide and 1,3-dimethyl-2-imidazolidinone.

The reaction temperature is preferably in the range of 0 to 150° C., more preferably 20 to 110° C.

The fluorine compound generated by the reaction can be isolated with ease by distillation from the reaction mixture. Further, bis-dialkylamino-difluoromethane can be recovered in the form of tetraalkylurea after finishing the reaction.

(4) Direct conversion of ketone oxygen into fluorine is an extremely useful method in the preparation of fluorine compounds, when the method is effective.

That is, a ketone compound having ketone group and represented by the formula (11):

wherein $R^{13}$ and $R^{14}$ are the same as above, is reacted with a fluorinating agent of the invention to prepare a fluorine compound represented by the formula (11-1):

wherein $R^{13}$ and $R^{14}$ are the same as above.

Any compound having a ketone group in the molecule can be used for the fluorination reaction as a ketone compound. Such ketone compounds are, for example, aryl ketone compounds and alkyl ketone compounds. However, no restriction is put upon these ketone compounds.

The amount of bis-dialkylamino-difluoromethane as a fluorinating agent is 1 equivalent or more for ketone.

No particular restriction is imposed upon the solvent for use in the reaction so long as the solvent does not react with the fluorinating agent, ketone compound and reaction product. Preferred solvents are acetonitrile, dichloromethane, chloroform, ethylene dichloride, 1,2-dimethoxyethane, diethyleneglycol dimethyl ether, N-methylpyrrolidinone, dimethylformamide and 1,3-dimethyl-2-imidazolidinone. The reaction temperature is preferably in the range of 0 to 150° C., more preferably 20 to 110° C. The fluorine compound formed by the reaction can be isolated with ease by distillation from the reaction mixture. The fluorinating agent can be recovered in the form of a corresponding urea compound after finishing the reaction.

(5) Fluorine substituted benzophenone prepared by fluorinating reaction of benzophenone which is a ketone compound, is generally used for the material of polyether ether ketone and other polyether ketone resins. Polyether ether ketone is a super engineering plastic and excellent in thermal resistance, electrical insulation, sliding property and chemical resistance. Fluorine substituted benzophenone is also used for a raw material or an intermediate of flame retardant, pain killer, platelet coagulation inhibitor and thrombosis inhibitor and thus is an important compound in the field of medicines and agricultural chemicals.

The fluorinating agent of the invention can directly fluorinate a hydroxy group of hydroxybenzophenone represented by the formula:

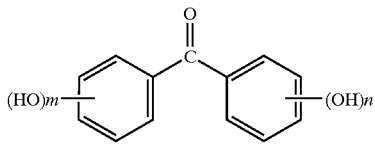

wherein m and n are an integer of 1 to 5 and are not simultaneously zero, to obtain fluorine substituted benzophenone:

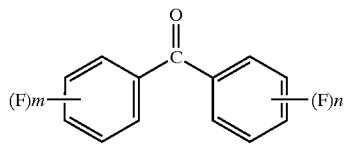

wherein m and n are the same as above.

Hydroxy substituted benzophenone which can be used in the process is 2-hydroxybenzophenone, 4-hydroxybenzophenone and other benzophenone derivatives having two phenyl groups which are arbitrarily selected from a 2-hydroxyphenyl, 4-hydroxyphenyl, 2,4-dihydroxyphenyl, 2,5-dihydroxyphenyl, 2,6-dihydroxyphenyl and 2,4,6-trihydroxyphenyl group.

The amount of a fluorinating agent is preferably 1 equivalent or more for the hydroxy group and desirably 1 to 10 equivalents in view of reaction efficiency unreacted hydroxy group remains when less than 1 equivalent is used.

No particular restriction is imposed upon the solvent for use in the reaction so long as the solvent does not react with the fluorinating agent, hydroxy substituted benzophenone compound and reaction product, fluorine substituted benzophenone compound. Preferred solvents are acetonitrile, dichloromethane, chloroform, ethylenedichloride, glyme, diglyme, N-methylpyrrolidone, N,N-dimethylformamide and 1,3-dimethyl-2-imidazolidinone.

The reaction temperature is preferably in the range of 0 to 150° C., more preferably 20 to 110° C. When the temperature is lower than 0° C., reaction velocity becomes slow and complex procedures are required. The reaction temperature exceeding 150° C. decreases stability of the fluorinating agent and tends to form by-products having a difluorinated ketone group. However, bis-fluorine substituted phenyldifluoromethane can be returned with ease to fluorine substituted benzophenone by means of hydrolysis.

The fluorine compound formed by the reaction can be isolated with ease from the reaction mixture by distillation, extraction and other procedures. The fluorinating agent used can be recovered in the form of corresponding urea after finishing the reaction.

(6) Conventionally, fluorinating agents which have been used for the conversion reaction of carboxylic acid into carbonyl fluoride have been $SF_4$ a four valent sulfur compound, and trifluorodiethylaminosulfur (hereinafter referred to simply as DAST).

$SF_4$ can directly convert carboxyl group into trifluoromethyl group. However, the converting reaction suffers from the defect that selection of optimum conditions is difficult and the yield is not so high [Org React., 21, 1 (1974)]. Furthermore, $SF_4$ itself is toxic and corrosive and has a problem of danger to explosion in the course of reaction. Further, DAST can efficiently fluorinate a carboxyl group to provide carboxylic acid fluoride, and is also useful as a fluorinating agent for a hydroxyl group of primary, secondary and tertiary alcohol, carbonyl group and other oxygen containing functional groups. However, DAST has problems on requirement for a specific manufacturing facility, high price and high danger to explosion.

The fluorinating agent of the invention can eliminate these problems and a fluorinating reaction of carboxylic acid can be carried out. Fluorine containing compounds thus obtained have been focused keen attention in recent years in the field of life science such as medicine and agricultural chemicals and also as a raw substance of functional materials.

Carboxylic acid fluoride can be prepared by using the fluorinating agent of the invention as follows.

That is, a compound having a carboxylic acid group represented by the formula (12):

$$R^{15}\text{—COOH} \tag{12}$$

wherein $R^{15}$ is the same as above, is reacted with a fluorinating agent of the invention to prepare acid fluoride represented by the formula (12-1):

$$R^{15}\text{—COF} \tag{12-1}$$

wherein $R^{15}$ is the same as above.

Representative carboxylic acids which can be used for the fluorination reaction include, for example, formic acid, acetic, propionic, butanoic, isobutanoic, pentanoic, 3-methyl-butanoic, pivalic, hexanoic, heptanoic, octanoic, nonanoic, decanoic, lauric, myristic, palmitic, stearic, phenylacetic, diphenylacetic, acetoacetic, phenylpropionic, cinnamic, oxalic, malonic, succinic, methylsuccinic, 1,5-pentanedicarboxylic, adipic, 1,7-heptane-dicarboxylic, suberic, azeloic, sebacic, dodecanedicarboxylic, eicosandicarboxylic and other aliphatic monocarboxylic and dicarboxylic acids; cyclohexanecarboxylic, 1-methyl-1-cyclohexanecarboxylic, 2-methyl-1-cyclohexanecarboxylic, 3-methyl-1-cyclohexanecarboxylic, 1,3-dicyclohexanedicarboxylic, 1,4-dicyclohexanedicarboxylic and other alicyclic mono- and di-carboxylic acids; benzoic, o-toluic, m-toluic, p-toluic, 4-isopropylbenzoic, 4-tert-butylbenzoic, o-methoxybenzoic, m-methoxybenzoic, p-methoxybenzoic, dimethoxybenzoic, trimethoxybenzoic, o-nitrobenzoic, m-nitrobenzoic, p-nitrobenzoic, phthalic, isophthalic, terephthalic and other aromatic monocarboxylic and dicarboxylic acids; and indole-2-carboxylic, indole-3-carboxylic, nicotinic and other heterocyclic carboxylic acids. However, no restriction is put upon these compounds. Acid fluoride compounds represented by the formula (12-1) can be individually obtained from corresponding carboxylic acid.

The amount of fluorinating agent is usually 1 equivalent or more for the carboxyl group.

The reaction is usually carried out in a solvent. No particular restriction is imposed upon the solvent so long as the solvent does not react with the fluorinating agent used and carboxylic acid fluoride formed. Preferred solvents are acetonitrile, dichloromethane, ethylenedichloride, dimethylformamide and 1,3-dimethyl-2-imidazolidinone.

The reaction temperature depends upon the solvent and reactivity of the carboxyl group and is usually in the range of −40 to 100° C., preferably −20 to 80° C. in view of the reaction velocity and depression of by-products. Carboxylic acid fluoride formed by the reaction can be isolated with ease from reaction mixture by distillation.

(7) Fluorination by way of a halogen exchange reaction

A process for preparing a fluorine compound from a halogen compound except fluorine compound by way of a halogen exchange reaction using metal fluoride, is a classical process. Other fluorinating agents which have been used are tetrabutylammonium fluoride (TBAF), TBAF HF, 70% HF-pyridine, and tris(dimethylamino)sulfonium-difluorotrimethylsilicate (TASF). However, TBAF is hygroscopic and decomposes at high temperature, and thus must be handled with caution. TASF has a problem of high price.

Application of the fluorinating agent of the invention enables effective syntheses of fluorinated compounds by a halogen exchange reaction. The reaction can exchange a halogen group of a compound with a fluorine group by using the fluorinating agent of the invention.

Aliphatic or aromatic compounds having a halogen group other than a fluorine group can be used for the object compound of the fluorinating reaction. However, a halogen group directly bonded to the aromatic ring can be more efficiently fluorinated with the fluorinating agent of the invention when one or more electrophilic substituents (for example, a nitro, carbonyl, cyano, trifluoromethyl or carboxyl group) are directly bonded to the aromatic ring.

A preferred example of the exchange reaction is a process for reacting an aromatic compound which has a halogen atom except fluorine and is represented by the formula (13):

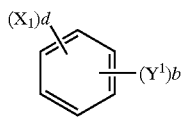

(13)

wherein $X_1$ is a halogen atom except fluorine, d is an integer of 1 to 5, Y is an electrophilic substituent, b is an integer of 1 to 5, and b+d $\leq$6, with the fluorinating agent of the invention to prepare a fluorine compound represented by the formula (13-1):

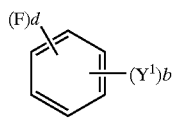

(13-1)

wherein $Y^1$, b and d are the same as in the formula (13).

Exemplary compounds which have a halogen group to be replaced by a fluorine group include, for example, 2,4-dinitrochlorobenzene, 4-chloronitrobenzene, 2-chloronitrobenzene, 2,3,4,5,6-pentachloronitrobenzene, 3,4,5,6-tetrachlorophthalic anhydride, 3,4,5,6-tetrachlorophthalyl chloride, 4,4'-dichloro-3,3'-dinitrobenzophenone, 4-chloro-trifluoromethylbenzene, 4-chloro-cyanobenzene and 4-bromobenzaldehyde. However, halogen compounds are not limited to the above compounds.

These halogen compounds individually provide a corresponding fluorine compounds represented by the formula (13-1).

The amount of the fluorinating agent is 1 equivalent or more, preferably 1 to 10 equivalents for a halogen group to be replaced by fluorine.

No particular restriction is imposed upon the solvent so long as the solvent does not react with the fluorinating agent, compounds having halogen groups and reaction products. Preferred solvents are acetonitrile, dichloromethane, chloroform, ethylene dichloride, 1,2-dimethyoxyethane, diethylene glycol dimethyl ether, N-methylpyrrolidinone, dimethylformamide and 1,3-dimethyl-2-imidazolidinone.

The reaction temperature is preferably in the range of 0 to 150° C., more preferably 20 to 110° C.

The fluorine compound formed by the reaction can be isolated with ease from the reaction mixture by means of distillation. The fluorinating agent can be recovered after hydrolysis in the form of corresponding urea.

(8) The fluorinating agent of the invention can be suitably used for preparing fluorine containing olefinic compounds. That is, the preparation process of fluorine containing olefinic compounds represented by the formula (25):

(25)

wherein $R^{15}$ to $R^{17}$ are a hydrogen atom or a lower alkyl group having to 3 carbon atoms and can be the same or different; and Z is —(Y)n—$CHF_2$, —(Y)n—$CHF_2$ or —CO—O—(Y)n$CH_2$F, wherein Y is —$CH_2$— and n is 0 or an integer of 1 to 5, comprises reacting a fluorinating agent represented by the formula (1) with olefinic compounds represented by the formula (24)

(24)

wherein $R^{15}$ to $R^{17}$ are a hydrogen atom or a lower alkyl group having 1 to 3 carbon atoms and can be the same or different; and X is —(Y)n—CHO, —(Y)n—$CH_2$OH, or —CO—O—(Y)n—$CH_2$OH wherein Y is —$CH_2$— and n is 0 or an integer of 1 to 5.

No particular restriction is imposed upon the olefins used in the invention.

Preferred olefinic compounds which can be used include an olefin species having an aldehyde group or the end of the molecule (the formula 26), an olefin species having a hydroxyl group on the molecular end (the formula 27) and olefinic ester having a hydroxyl group on the molecular end (the formula 28).

(26)

(27)

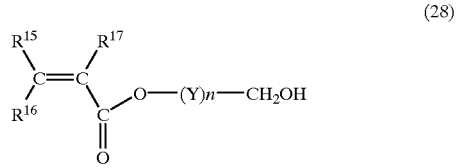

(28)

wherein $R^{15}$ to $R^{17}$ and Y are the same as above.

These olefinic compounds are fluorinated the —CHO group into the —$CHF_2$ group and the —$CH_2$OH group into the $CH_2$F group, respectively, and individually provide the fluorine containing olefinic compounds which correspond to the above formulas (26), (27) and (28).

On the fluorination reaction between the fluorinating agent represented by the formula (1) and the olefinic compound having an aldehyde group represented by the formula (26), the amount of bis-dialkylamino-difluoromethane is preferably 1 equivalent or more for the aldehyde group. when the fluorination reaction is carried out on the olefinic compounds having a hydroxyl group represented by the formula (27) or (28). The amount of bis-dialkylamino- (9) The fluorinating agent of the invention can be applied to the preparation of fluorine containing diaminobenzophenone and fluorine containing diamino-diphenylmethane which are useful for a monomer of polyimide.

That is, below described compounds can be prepared from 3,3'-dinitro-4,4'-dichlorobenzophenone which is available with ease in industry.

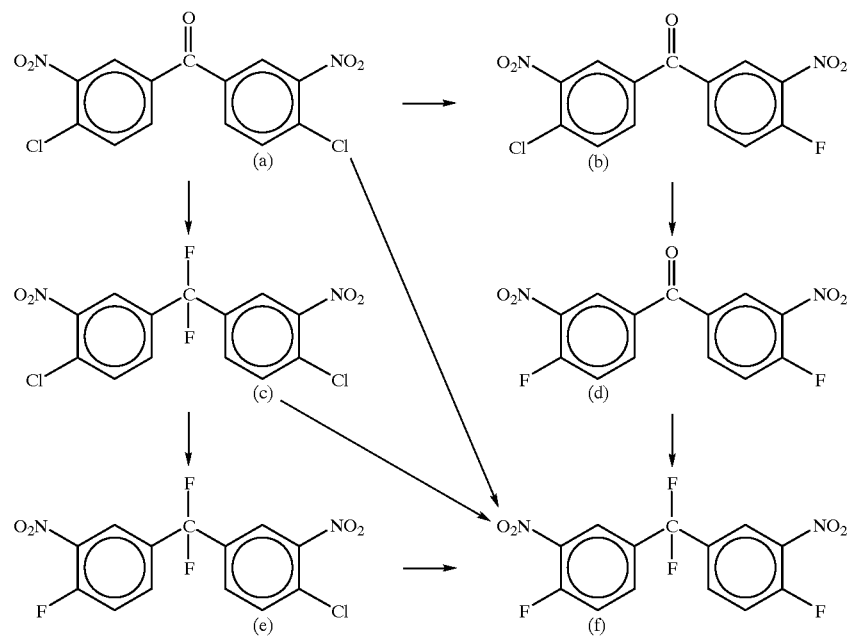

difluoromethane is preferably 1 equivalent or more for the hydroxyl group.

No particular restriction is imposed upon the solvent so long as the solvent is inert and does not react with bis-dialkylamino-difluoromethane and olefinic compounds having an aldehyde group or a hydroxy group. Preferred solvents are acetonitrile, dichloromethane, chloroform, ethylene dichloride, glyme, diglyme, N-methyl-pyrrolidinone, dimethylformamide and 1,3-dimethyl-2-imidazolidinone.

No particular limitation is imposed upon the amount of the amount of the solvent. However, the amount is preferably 1 to 10 times by weight for the substrate in view of reaction efficiency and operation ability. On carrying out the reaction, base such as tertiary amine is preferably added in order to capture generated hydrogen fluoride.

No particular limitation is put upon the reaction temperature. However, in the case of an olefin compound having an aldehyde group, the temperature is in the range of 0 to 150° C., preferably 20 to 110° C. in view of reaction velocity and stability of product. In the case of an olefin compound having a hydroxyl group, the temperature is in the range of -40 to 100° C., preferably -20 to 80° C. When elimination of hydrogen fluoride is a competitive reaction, the reaction is preferably carried out at low temperature as possible.

The fluorine compound formed by the reaction can be removed with ease from the reaction mixture by means of distillation. Bis-dialkylamino-difluoromethane can be recovered in the form of tetraalkylurea after finishing the reaction.

Use of the fluorinating agent in the invention enables to prepare desired fluorine compounds with suitable conditions. As shown above by the formulas (a) to (f), 3,3'-dinitro-4,4'-dichlorobenzophenone (a) is used for preparing 4-chloro-4'-fluoro-3,3'-dinitrobenzophenone (b), bis(3-nitro-4-chlorophenyl)difluoromethane (c), 3,3'-dinitro-4,4'-difluorobenzophenone (d), 4-chloro-4'-fluoro-3,3'-dinitrophenyldifluoromethane (e),and bis(3-nitro-4-fluorophenyl)difluoromethane (f).

A compound having larger numbers of the substituted fluorine groups can be obtained with increase in the mol ratio of the fluorinating agent to 3,3 '-dinitro-4,4'-dichloro benzophenone. Further, a compound having a large number of the fluorine group can also be obtained by preparing a compound having a less number of the fluorine group and reacting the compound with the fluorinating agent.

For example, the fluorine compound (f) can be prepared by using 2 equivalent or more fluorinating agent for the raw material compound (a).

The reaction shows that the direct conversion of ketone oxygen in the above (4) into fluorine and the fluorinating reaction by way of an exchange reaction of halogen which is substituted on the aromatic ring in the above (7) can progress with ease by the fluorinating agent of the invention. The solvent, reaction temperature and other conditions are in accordance with the reaction conditions in the above (4) and (7).

The reaction shown in (8) is one of the preferred embodiments for using the halogenating agent of the invention in the halogenation of compounds having a ketone or halogen group.

Next, the halogenating agent of the formula (15) will be illustrated.

The halogenating agent of the invention is a compound represented by the formula (15):

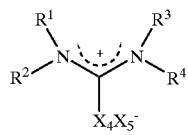

(15)

In the formula (15), $X_4$ and $X_5$ are the same or different halogen atoms except that both $X_4$ and $X_5$ are not simultaneously fluorine atoms, chlorine atoms or bromine atoms.

The combination of $X_4$ and $X_5$ are F—Cl, F—Br, F—I, Cl—Br, Cl—I and I—I. Additionally, when halogen atoms of $X_4$ and $X_5$ are different, the atom having a lower atomic weight is liable to form a covalent bond and the atom having a higher atomic weight tends to form an ion pair.

$R^1$ to $R^4$ are same or different, substituted or unsubstituted, saturated or unsaturated alkyl group or substituted or unsubstituted aryl group. $R^1$ and $R^2$ or $R^3$ and $R^4$ can bond to form a ring including a nitrogen atom or a nitrogen atom and other hetero atoms. $R^1$ and $R^3$ can bond to form a ring including a nitrogen atom or a nitrogen atom and other hetero atoms. Preferred alkyl or aryl group has preferably 1 to 6 carbon atoms. Alkyl group is straight or branched, that is, a methyl group, ethyl, n-propyl, allyl, isopropyl, n-butyl, butenyl, n-hexyl or phenyl group and can be the same or different.

Further, $R^1$ and $R^2$ or $R^3$ and $R^4$ can respectively bond to form a heterocyclic ring having a nitrogen atom and 3 to 5 carbon atoms. Examples of such rings are pyrrolidine ring and piperidine ring.

Further, $R^1$ and $R^3$ can bond to form a five- or six-membered heterocyclic ring including two nitrogen atoms such as an imidazolidine ring, imidazolidinone ring, pyrimidine ring and pyrimidinone ring.

Preferred practical examples of the halogenating agent represented by the formula (15) include following compounds. However, the scope of the invention is not restricted by these exemplified halogenating agents.

Exemplary chlorinating agents include:
tetramethyl-2-fluoroformamidinium=chloride,
tetraethyl-2-fluoroformamidinium=chloride,
tetra-n-propyl-2-fluoroformamidinium=chloride,
tetraisopropyl-2-fluoroformamidinium=chloride,
tetra-n-butyl-2-fluoroformamidinium=chloride,
tetra-n-pentyl-2-fluoroformamidinium=chloride,
tetra-n-hexyl-2-fluoroformamidinium=chloride,
2-fluoro-1,3-dimethylimidazolinium=chloride,
2-fluoro-1,3-diethylimidazolinium=chloride,
2-fluoro-1,3-di-n-propylimidazolinium=chloride,
2-fluoro-1,3-di-n-butylimidazolinium=chloride,
2-fluoro-1,3-di-n-pentylimidazolinium=chloride,
2-fluoro-1,3-di-n-hexylimidazolinium=chloride,
N,N-dimethyl-N',N'-methylphenyl-fluoroformamidinium=chloride, and
fluoro-bis(1-piperidyl)methylium=chloride.

Exemplary brominating agents include:
tetramethyl-2-fluoroformamidinium=bromide,
tetraethyl-2-fluoroformamidinium=bromide,
tetra-n-propyl-2-fluoroformamidinium=bromide,
tetraisopropyl-2-fluoroformamidinium=bromide,
tetra-n-butyl-2-fluoroformamidinium=bromide,
tetra-n-pentyl-2-fluoroformamidinium=bromide,
tetra-n-hexyl-2-fluoroformamidinium=bromide,
2-fluoro-1,3-diethylimidazolinium=bromide,
2-fluoro-1,3-diethylimidazolinium=bromide,
2-fluoro-1,3-di-n-propylimidazolinium=bromide,
2-fluoro-1,3-di-n-butylimidazolinium=bromide,
2-fluoro-1,3-di-n-pentylimidazolinium=bromide,
2-fluoro-1,3-di-n-hexylimidazolinium=bromide,
N,N-dimethyl-N',N'-dimethylphenyl-fluoroformamidinium=bromide,
fluoro-bis(1-piperidyl)methylium=bromide,
tetramethyl-2-chloroformamidinium=bromide,
tetraethyl-2-chloroformamidinium=bromide,
2-chloro-1,3-dimethylimidazolinium=bromide and
2-chloro-1,3-diethylimidazolinium=bromide.

Exemplary iodinating agents include:
tetramethyl-2-fluoroformamidinium=iodide,
tetraethyl-2-fluoroformamidinium=iodide,
tetra-n-propyl-2-fluoroformamidinium=iodide,
tetraisopropyl-2-fluoroformamidinium=iodide,
tetra-n-butyl-2-fluoroformamidinium=iodide,
tetra-n-pentyl-2-fluoroformamidinium=iodide,
tetra-n-hexyl-2-fluoroformamidinium=iodide,
2-fluoro-1,3-diethylimidazolinium=iodide,
2-fluoro-1,3-diethylimidazolinium=iodide,
2-fluoro-1,3-di-n-propylimidazolinium=iodide,
2-fluoro-1,3-di-n-butylimidazolinium=iodide,
2-fluoro-1,3-di-n-pentylimidazolinium=iodide,
2-fluoro-1,3-di-n-hexylimidazolinium=iodide,
N,N-dimethyl-N',N'-dimethylphenyl-fluoroformamidinium=iodide,
fluoro-bis(1-piperidyl)methylium=iodide,
tetramethyl-2-chloroformamidinium=iodide,
tetraethyl-2-chloroformamidinium=iodide,
2-chloro-1,3-dimethylimidazolinium=iodide,
2-chloro-1,3-diethylimidazolinium=iodide,
tetramethyl-2-iodoformamidinium=iodide,
tetraethyl-2-iodoformamidinium=iodide,
2-iodo-1,3-dimethylimidazolinium=iodide,
2-iodo-1,3-diethylimidazolinium=iodide.

Tetraalkyl-fluoroformamidinium=halide is a preferable compound and can react with alcohol in a very mild condition to obtain a halogen compound resulting from exchanging the counter ion ($X_5$) with an alcoholic hydroxyl group on the compound represented by the formula (15).

Particularly preferred compounds are:
2-fluoro-1,3-dimethylimidazolinium=chloride represented by the formula (18):

(18)

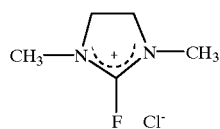

2-fluoro-1,3-dimethylimidazolinium=bromide represented by the formula (19):

(19)

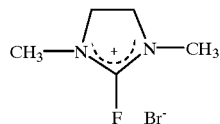

2-fluoro-1,3-dimethylimidazolinium=iodide represented by the formula (20):

(20)

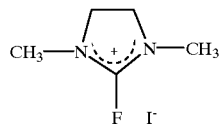

2-chloro-1,3-dimethylimidazolinium=bromide represented by the formula (21):

(21)

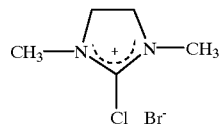

2-chloro-1,3-dimethylimidazolinium=iodide represented by the formula (22):

(22)

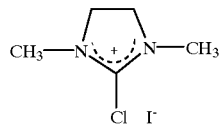

2-iodo-1,3-dimethylimidazolinium=iodide represented by the formula (23):

(23)

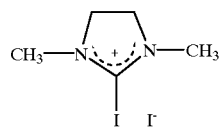

These halogenating agents can be applied to the above various halogenating reactions of the invention.

Desired halogen compounds can be obtained by carrying out the desired halogenating reaction with a suitable halogenating agent according to the above reaction, respectively.

For example, halogenating of an alcoholic hydroxyl group with these halogenating agents can selectively provide a halogen compound of the counter ($X_5$) on the formula (15).

That is, an alcoholic hydroxyl group containing compound represented by the formula (8):

$$R^{11}\text{—OH} \qquad (8)$$

wherein $R^{11}$ is a substituted or unsubstituted alkyl group and can include an unsaturated group therein, is reacted with the halogenating agent represented by the formula (15):

(15)

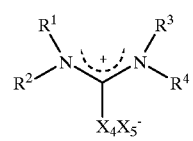

wherein $X_4$, $X_5$, and $R^1$ to $R^4$ are the same as above, to prepare a halogen compound represented by the formula (8-2):

$$R^{11}\text{—}X_5 \qquad (8\text{-}2)$$

wherein $R^{11}$ is a substituted or unsubstituted alkyl group and can include anunsaturated group therein and $X_5$ is a halogen atom.

Exemplary alcoholic hydroxyl compounds which can be utilized for the reaction include methyl alcohol, ethyl, n-propyl, n-butyl, isobutyl, 2-methylbutyl, n-amyl, neoamyl, isoamyl, n-hexyl, 2-methylpentyl, 2-ethylbutyl, n-nonyl, 3,5,5-trimethylhexyl, n-decyl, n-undecyl, n-dodecyl, allyl, methallyl, crotyl, benzyl, phenetyl, cinnamyl, propargyl alcohol and other primary alcohols ; and isopropyl, sec-butyl, sec-amyl, sec-isoamyl, 1-ethylpentyl, 1,3-dimethylbutyl, 1-methylhexyl, 1-ethylpentyl, 1-ethylpropyl, 4-methyl-2-pentyl, 1-methylhexyl, 1-ethylpentyl, 1-methylheptyl, cyclohexyl, 2-methylcyclohexyl, 3-methylcyclohexyl, 4-methylcyclohexyl, sec-phenetyl alcohol and other secondary alcohols ; and tert-butyl, tert-amyl, 1-methylcyclohexyl, α-terpin alcohol and other tertiary alcohols. However, alcoholic hydroxyl compounds are not restricted to these compounds.

The amount of the halogenating agent is usually 1 equivalent or more for an alcoholic hydroxyl group. No particular restriction is imposed upon the solvent so long as the solvent does not react with the reaction substrate, reaction agent and reaction product. The solvent is preferably acetonitrile, dichloromethane, ethylene dichloride, glyme, diglyme, dimethylformamide, 1,3-dimethyl-2-imidazolidinone, benzene, toluene and hexane.

The reaction temperature is usually −40 to 100° C., preferably −20 to 80° C. Formed products can be isolated with ease from the reaction mixture by means of distillation.

Further, the reaction can be carried out in the presence of a hydrogen halogenide capturing agent, base and acid catalyst so long as these materials give no adverse effect on the halogenating agent represented by the formula (15), oxygen containing functional compound and reaction product.

The halogen compound formed by the reaction can be isolated with ease from the reaction mixture by means of distillation. When the compound represented by the formula (15) remains unreacted, generated hydrogen halogenide can be caught by addition of sodium hydrogen carbonate.

Furthermore, the halogenating agent represented by the formula (15) can be recovered in the form of corresponding urea after finishing the reaction.

Carboxylic acid halogenides represented by the formula (12-2):

$$R^{15}\text{—}COX_6 \qquad (12\text{-}2)$$

wherein $R^{15}$ is a substituted or unsubstituted, saturated or unsaturated alkyl group or substituted or unsubstituted aryl group and $X_6$ is a halogen atom represented by $X_4$ or $X_5$ in the formula (15) which can prepared by reacting a carboxylic acid compound represented by the formula (12):

$$R^{15}\text{—}COOH \qquad (12)$$

wherein $R^{15}$ is the same as in the formula (12-2), with the above halogenating agent represented by the formula (15).

The resulting carboxylic acid halide group has a halogen atom which individually corresponds to $X_4$ and $X_5$ in the formula (15). When $X_4$ is F and $X_5$ is Br on the formula (15) of the halogenating agent, carboxylic acid bromide, carboxylic acid fluoride and carboxylic acid anhydride are formed, and carboxylic acid fluoride has the highest selectivity.

When $X_4$ is F and $X_5$ is I on the formula (15) of the halogenating agent, carboxylic acid fluoride and carboxylic acid anhydride are formed, and carboxylic acid fluoride has the higher selectivity. Formation of carboxylic acid iodide cannot be confirmed.

Representative compounds which have a carboxyl group and can be used for the reaction include, for example, formic acid, acetic, propionic, butanoic, isobutanoic, pentanoic, 3-methylbutanoic, pivalic, hexanoic, heptanoic, octanoic, nonanoic, decanoic, lauric, myristic, palmitic, stearic, phenylacetic, diphenylacetic, acetoacetic, phenylpropionic, cinnamic, oxalic, malonic, succinic, methylsuccinic, 1,5-pentanedicarboxylic, adipic, 1,7-heptanedicarboxylic, suberic, azelaic, sebacic, dodecanedicarboxylic, eicosanedicarboxylic acid and other aliphatic monocarboxylic and dicarboxylic acids; cyclohexylcarboxylic, 1-methyl-1-cyclohexylcarboxylic, 2-methyl-1-cyclohexylcarboxylic, 3-methyl-1-cyclohexylcarboxylic, 1,3-dicyclohexyldicarboxylic, 1,4-dicyclohexylcarboxylic acid and other alicyclic monocarboxylic and dicarboxylic acids; benzoic, o-toluic, m-toluic, p-toluic, 4-isopropylbenzoic, 4-tert-butylbenzoic, o-methoxybenzoic, m-methoxybenzoic, p-methoxybenzoic, dimethoxybenzoic, trimethoxybenzoic, o-nitrobenzoic, m-nitrobenzoic, p-nitrobenzoic, phthalic, isophthalic, terephthalic acid and other aromatic monocarboxylic and dicarboxylic acids; indole-2-carboxylic, indole-3-carboxylic, nicotinic acid and other heterocyclic carboxylic acids. However, carboxyl compounds are not limited to these compounds.

The amount of halogenating agents is usually 1 equivalent or more for the carboxyl group. No particular restriction is imposed upon the solvent so long as the solvent does not react with reaction substrates, reaction agents and formed products. Preferred solvents are acetonitrile, dichloromethane, ethylene-dichloride, glyme, diglyme, dimethylformamide, 1,3-dimethyl-2-imidazolidinone, benzene and toluene.

The reaction temperature is usually –40 to 100° C., preferably –20 to 80° C. Formed products can be isolated with ease from the reaction mixture by means of distillation.

Further, a hydrogen halogenide capturing agent, base and acid catalyst can be added to the reaction system so long as these materials give no adverse effect on the halogenating agent represented by the formula (15), oxygen containing functional compound and reaction product.

The halogen compound formed by the reaction can be isolated with ease from the reaction mixture by means of distillation.

When the compound represented by the formula (15) remains unreacted, generated hydrogen halogenide can be caught by addition of sodium hydrogen carbonate.

Furthermore, the halogenating agent represented by the general formula (15) can be recovered in the form of corresponding urea after finishing the reaction.

Fluorine compound represented by the formula (10-2):

$$R^{12}\text{—}CH(X_7)_2 \qquad (10\text{-}2)$$

wherein $R^{12}$ is a substituted or unsubstituted, saturated or unsaturated alkyl group or a substituted or unsubstituted aryl group and $X_7$ is the halogen atom represented by $X_4$ or $X_5$ in the formula (15) and two $X^7$'s are not simultaneously same, can be prepared by reacting an aldehyde compound represented by the formula (10):

$$R^{12}\text{—}CHO \qquad (10)$$

wherein $R^{12}$ is the same as in the formula (10-2), with a halogenating agent the above halogenating agent.

When a halogenating agent having F on $X_4$ and Cl on $X_5$ in the formula (15) is used for halogenation of a formyl group, conversion of the formyl group into a chlorofluoromethyl group and dichloromethyl group is observed. In the case, the chlorofluoromethyl group can be obtained in higher selectivity.

Exemplary compounds having a halogenatable formyl group include, for example, form-aldehyde, aceto, propio, butyl, isobutyl, valer, isovaler, hexa, hept, octyl, nonyl, decylaldehyde and other aliphatic aldehydes; benz, p-nitrobenz, anisic, phthalic, naphthoaldehyde and other aromatic aldehyde; cyclohexanecarboxyaldehyde and other alicyclic aldehydes; and nicotinic aldehyde, furfural and other heterocyclic aldehydes. However, aldehyde compounds are not limited to these compounds.

The amount of halogenating agent is usually 1 equivalent or more for a formyl group. No particular restriction is imposed upon the solvent so long as the solvent dose not react with reaction substrates, reaction agents and reaction products. Preferred solvents are acetonitrile, dichloromethane, ethylene dichloride, glyme, diglyme, dimethylformamide, 1,3-dimethyl-2-imidazolidinone, benzene and toluene.

The reaction temperature is usually 0 to 150° C., preferably 20 to 110° C. The reaction product can be isolated with ease from the reaction mixture by means of distillation.

Further, the reaction can be carried out in the presence of a hydrogen halogenide capturing agent, base and acid catalyst so long as these materials give no adverse effect on the halogenating agents represented by the formula (15), oxygen containing functional compounds and reaction products.

The halogenated compounds formed by the reaction can be isolated with ease from the reaction mixture by means of distillation. When the halogenating agent represented by the formula (15) remains unreacted, generated hydrogen halogenide can be caught by addition of sodium hydrogen carbonate.

Further, the halogenating agent represented by the formula (15) can be recovered in the form of corresponding urea after finishing the reaction.

These halogenating agents represented by the formulas (15) to (17) can be safely prepared with ease by carrying out a halogen exchange reaction of a compound represented by the formula (14):

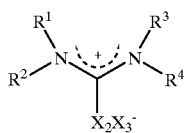

(14)

wherein $X_2$ and $X_3$ are a chlorine or bromine atoms; $R^1$ to $R^4$ are a substituted or unsubstituted, saturated or unsaturated alkyl group, or a substituted or unsubstituted aryl group and can be the same or different; $R^1$ and $R^2$ or $R^3$ and $R^4$ can bond to form a ring including a nitrogen atom or a nitrogen atom and other hetero atoms; or $R^1$ and $R^3$ can bond to form a ring including a nitrogen atom or a nitrogen atom and other hetero atoms, with an alkali metal salt of desired halogen in an inert solvent.

The compound represented by the formula (15) can be used as intact for a chlorinating agent or a brominating agent. However, in order to obtain a halogenating agent having high reactivity, tetraalkyl-2-fluoroformamidinium= chloride is prepared by reacting with an alkali metal salt of fluorine such as cesium fluoride, rubidium fluoride, potassium fluoride or sodium fluoride and can be used as a chlorinating agent or a brominating agent.

In order to prepare a brominating agent from a compound having chlorine atoms on the positions of $X_2$ and $X_3$, sodium bromide, potassium bromide and other alkali metal salts of bromine can be used.

When an iodating agent is desired, cesium iodide, rubidium iodide, potassium iodide and sodium iodide can be used.

The halogenating agent represented by the formula (15) is prepared from the compound represented by the formula (14) which is prepared as mentioned above.

On the preparation of a halogenating agent represented by the formula (15) in the invention, the amount of the alkali metal salt of halogen used for the halogen exchange reaction is preferably 2 equivalents or more, more preferably 2 to 5 equivalents for the compound represented by the formula (14). When the amount is less than 2 equivalents, unexchanged chloride remains unsatisfactorily. On the other hand, the amount exceeding 5 equivalents does not improve the yield so much.

No particular restriction is imposed upon the solvent used for the halogen exchange reaction so long as the solvent does not react with the compound represented by the formula (14) and reaction product. Preferred solvents are acetonitrile, dimethylformamide, 1,3-dimethyl-2-imidazolidinone, dichloromethane and ethylene dichloride.

No particular limitation is put upon the amount of the solvent. However, in view of reaction efficiency and operation ability, preferred amount is 1 to 10 times by weight for the reaction substrate.

The reaction temperature is usually in the range of −20 to 150° C., preferably 0 to 100° C. in view of reaction velocity and stability of the formed compound. The iodating agent is prepared preferably in the range of 0 to 80° C. in a nitrogen atmosphere under light shielding in order to inhibit oxidation of the iodating agent.

The above halogen exchange reaction can also be carried out in the coexistence of a phase transfer catalyst such as quaternary alkyl ammonium salt and quaternary alkyl phosphonium salt. The reaction mixture containing the resultant halogenating agent represented by the formula (15) can be used for the next halogenating reaction as is or after filtering the inorganic salt and distilling off the solvent.

The halogenating agent represented by the above formula (15) also can be prepared by carrying out a halogen exchange reaction of the fluorinating agent represented by the formula (1) of the present invention with an alkali metal salt of chlorine, bromine or iodine atom in the inert solvent.

The reaction can be carried out by almost the same reaction condition as the above mentioned the halogen exchange reaction.

The invention will hereinafter be illustrated further in detail by way of examples. However, these examples do not limit the scope of the invention. In Example 1 the concentration of 2,2-difluoro-1,3-dimethylimidazolidine (hereinafter referred to simply as DFI) in an acetonitrile solution was measured by high performance liquid chromatography (hereinafter referred to simply as HPLC method) after converting into a derivative by reacting with aniline. Fluorine ion (hereinafter referred to simply as F-) concentration was measured by absorptiometry using an alizarin complexing reagent.

EXAMPLE 1

Synthesis of 2,2-difluoro-1,3-dimethyl-imidazolidine(DFI)

To a 500 ml four necked reaction flask, 76.4 g (0.452 mol) of 2-chloro-1,3-dimethyl-imidazolinium=chloride, 105.2 g (1.810 mol) of spray dried potassium fluoride, and 320 ml of acetonitrile were charged, and reacted in a nitrogen atmosphere at 80° C. for 17 hours. After cooling the reaction mixture to 25° C., inorganic salts were separated from the reaction mixture to obtain 414.2 g of an acetonitrile solution of DFI(MW 136.15). DFI concentration in the solution was 11.4 wt %. The yield was 77%.

The reaction mixture was vacuum distilled to obtain 32 g of DFI having purity of 97.8%. DFI had following properties.

Boiling point 47.0° C./37 mmHg, EIMS: 136 ($M^+$), 117 ($M^+$−$F^+$), IR(neat)cm$^{-1}$: 1486, 1385, 1295, 1242, 1085, 966, 711, F-analysis: Calculated 27.9%, Found 27.7%, $^1$H-NMR (δ, ppm, CDCl$_3$, TMS basis): 2.52(s, 6H, —CH$_3$×2), 3.05(s, 4H, —CH$_2$CH$_2$—), $^{13}$C NMR (δ, ppm, CDCl$_3$, −45° C. CDCl$_3$ basis): 31.4(s, —CH$_3$×2), 47.6(s, —CH$_2$CH$_2$—), 128.5(t, J=230 Hz, =CF$_2$), $^{19}$F NMR(δ, ppm, CDCl$_3$, −45° C. CFCl$_3$ basis): −70.9(s, =CF$_2$). IR spectrum diagram is shown in FIG. 1.

EXAMPLE 2

Synthesis of bis-dimethylamino-difluoro-methane (Hereinafter Referred to Simply as TMF)

To a solution of 33.32 g (0.224 mol) of tetramethylchloroformamidinium=chloride in 107.82 g of acetonitrile, 52.06 g (0.896 mol) of spray dried potassium fluoride and 33.66 g of acetonitrile were added and reacted at 85° C. for 52 hours. Successively, the reaction mass was filtered to obtain an acetonitrile solution of TMF. Properties of TMF were measured by using the acetonitrile solution. Properties are as follows.

EIMS: 138($M^+$), 119 ($M$−$F$)$^+$, F-analysis: Calculated 12.4%, Found 12.1%, $^1$H-NMR (δ, ppm, CH$_3$CN solvent, CH$_3$CN basis, 24° C.): 2.44(s, —CH$_3$), $^{13}$C NMR (δ, ppm, CH$_3$CN solvent, 24° C. DMSO-d$_6$ basis): 36. 1(s, —CH$_3$× 4), 128.6(t, =CF$_2$).

EXAMPLE 3

Synthesis of bis-di-n-butylamino-difluoro-methane (Hereinafter Referred to Simply as TBF)

To a solution of 74.36 g (0.2129 mol) of tetra-n-butyl-chloroformamidinium=chloride in 181.45 g of acetonitrile, 50.92 g (0.8864 mol) of spray dried potassium fluoride and 7.86 g of acetonitrile were added and reacted at 85 for 35 hours. Thereafter, the reaction mass was filtered. The filtrate was separated into two layers. The two layers were mixed and acetonitrile was distilled off under reduced pressure. The resulting residue was TBF. The residue had following properties.

EIMS: 306($M^+$), 287 $(M-F)^+$, F-analysis: Calculated 12.4%, Found 12.1%, $^1$H-NMR ($\delta$, ppm, No solvent dilution, $CH_3CN$ basis, 24° C.: 1.04 (tj=~8 Hz, $CH_2\underline{CH}_3$), 1.41 (m, j=~8 Hz, $CH_2\underline{CH}_2CH_3$), 1.59 (quint, j=~8 Hz, $CH_2\underline{CH}_2CH_2$), 2.92 (t, j=~8 Hz, $N\underline{CH}_2CH_2$), $^{13}$C NMR ($\delta$, ppm, No solvent dilution, 24° C., DMSO-$d_6$ basis): 12.8 ($CH_2\underline{CH}_3$), 19.6 ($CH_2\underline{CH}_2CH_3$), 30.2 ($CH_2\underline{CH}_2CH_2$), 46.3 ($N\underline{CH}_2CH_2$), 128.2(t, j=248 Hz, $CF_2$).

EXAMPLE 4

Synthesis of 2,2-difluoro-1,3-di-n-butyl-imidazolidine (Hereinafter Referred to Simply as DFB)

To a reaction vessel, 51.7 g (0.184 mol) of 2-chloro-1,3-di-n-butyl-imidazolinium=chloride having purity of 90%, 174 g of acetonitrile and 64.3 g (1.11 mol) of spray dried potassium fluoride were charged and reacted at 85° C. for 25 hours under slightly increased pressure of nitrogen. After cooling, the reaction mass was filtered to obtain an acetonitrile solution of DFB. Properties were measured by using the solution.

$^1$H-NMR ($\delta$, ppm, $CDCl_3$, TMS basis, 25° C.): 0.93(t, j=~8 Hz, $C_2\underline{CH}_3$), 1.40 (m, j=~8 Hz, $CH_2\underline{CH}_2CH_3$), 1.56 (quint, j=~8 Hz, $CH_2\underline{CH}_2CH_3$), 2.95 (t, j=~8 Hz, $N\underline{CH}_2CH_2$), 3.24(s, $NCH_2\underline{CH}_2N$), $^{13}$C NMR($\delta$, ppm, $CDCl_3$, –65° C. $CDCl_3$ basis): 13.4 (s, $CH_2\underline{CH}_3$), 19.4 (s, $CH_2\underline{CH}_2CH_3$), 29.1(s, $CH_2\underline{CH}_2CH_2$), 45.1(s, $N\underline{CH}_2CH_2CH_2$), 45.5 (s, $NCH_2\underline{CH}_2N$), 128.9 (t, j=228 Hz, $CF_2$).

EXAMPLE 5

Synthesis of Benzoyl Fluoride

To a reaction vessel, 23.89 g (0.02 mol) of a 11.4 wt % solution of DFI in acetonitrile which was obtained by similar procedures as Example 1, 2.44 g (0.02 mol) of benzoic acid and 8 ml of acetonitrile were charged and reacted at 25° C. for 4 hours in a nitrogen atmosphere. After finishing the reaction, a portion of the reaction mixture was taken out and a GC-MS measurement was carried out. As a result, formation of benzoyl fluoride (master ion, 124) was confirmed. The yield of the reaction was 98% by GC analysis.

COMPARATIVE EXAMPLE 1

Synthesis of Benzoyl Fluoride

To a reaction vessel, 0.79 g (3.0 mol) of 2-fluoro-1,3-dimethyl-imidazolinium=hexafluorophosphate obtained in accordance with a preparation process described in WO96/04297, 0.24 g (2.0 mol) of benzoic acid and 15 ml of acetonitrile were charged and reacted at 25° C. for 4 hours in a nitrogen atmosphere. After finishing the reaction, GC analysis was carried out on the reaction mixture. As a result, benzoyl fluoride was formed in the yield of 77%.

EXAMPLE 6

Synthesis of Benzyl Fluoride

To a reaction vessel, 1.783 g (1.50 m mol) of a 11.4 wt % solution of DFI in acetonitrile which was obtained by similar procedures as Example 1, 0.162 g (1.50 m mol) of benzyl alcohol and 6 ml of acetonitrile were charged and reacted at 25° C. for 4 hours in a nitrogen atmosphere. After finishing the reaction, a GC-MS measurement was carried out on the reaction mixture. As a result, formation of benzyl fluoride (master ion, 110) was confirmed. The yield of the reaction was 83% by GC analysis.

COMPARATIVE EXAMPLE 2

Synthesis of Benzyl Fluoride

To a reaction vessel, 0.40 g (1.5 m mol) of 2-fluoro-1,3-dimethyl-imidazolinium=hexafluorophosphate obtained in accordance with a preparation process described in WO96/04297, 0.162 g (1.5 m mol) of benzyl alcohol and 6 ml of acetonitrile were charged and reacted at 25° C. for 4 hours in a nitrogen atmosphere. Thereafter GC analysis was carried out on the reaction mixture. As a result, benzyl fluoride was not detected.

EXAMPLE 7

Synthesis of n-octyl Fluoride

To a reaction vessel, 1.79 g (1.50 m mol) of a 11.4 wt % solution of DFI in acetonitrile which was obtained by the same procedures as Example 1, 0.195 g (1.50 m mol) of n-octyl alcohol and 4 ml of acetonitrile were charged and reacted at 25° C. for 4 hours in a nitrogen atmosphere. After finishing the reaction, GC-MS measurement was carried out on the reaction mixture. Formation of n-octyl fluoride (master ion, 132) was confirmed. The yield was 80%.

EXAMPLE 8

Synthesis of n-octyl Fluoride

To a reaction vessel, 4.15 g (5.29 m mol) of a 17.56 wt % solution of TMF in acetonitrile which was prepared in Example 2, 0.275 g (2.55 m mol) of n-octyl alcohol and acetonitrile were charged and reacted at 25 for 4 hours in a nitrogen atmosphere. After finishing the reaction, formation of n-octyl fluoride (master ion, 132) was confirmed by GC-MS measurement on the reaction mixture. The yield of the reaction was 96% by GC analysis.

EXAMPLE 9

Synthesis of n-octyl Fluoride

To a reaction vessel, 0.9 g (2.9 m mol) of TBF having purity of 91% which was prepared in Example 3, 0.15 g (1.15 m mol) of n-octyl alcohol and 6 ml of acetonitrile were charged and reacted at 25° C. for 4 hours in a nitrogen atmosphere. After finishing the reaction, formation of n-octyl fluoride (master ion, 132) was confirmed by GC-MS measurement on the reaction mixture. The yield of the reaction was 98.2% by GC analysis.

EXAMPLE 10

Synthesis of n-octyl Fluoride

To a reaction vessel, 1.61 g (0.77 m mol) of DFB having purity of 13% which was prepared in Example 4, 0.12 g (0.77 m mol) of n-octyl alcohol and 2 ml of acetonitrile were charged and reacted at 25° C. for 1 hour in a nitrogen atmosphere. After finishing the reaction, formation of n-octyl fluoride (master ion, 132) was confirmed by GC-MS measurement on the reaction mixture. The yield of the reaction was 90% by GC analysis.

COMPARATIVE EXAMPLE 3

Synthesis of n-octyl Fluoride

To a reaction vessel, 0.40 g (1.5 m mol) of 2-fluoro-1,3-dimethyl-imidazolinium=hexafluorophosphate which was prepared in accordance with the preparation process described in WO96/04297, 0.195 g (1.5 m mol) of n-octyl alcohol and 6 ml of acetonitrile were charged and reacted at 25° C. for 4 hours in a nitrogen atmosphere. Thereafter, GC analysis was carried out on the reaction mixture. n-Octyl fluoride was not detected.

EXAMPLE 11
Synthesis of t-amyl Fluoride

To a reaction vessel, 7.74 g (6.48 m mol) of a 11.4 wt % DFI solution in acetonitrile which was obtained by the same procedures as Example 1, and 0.285 g (3.24 m mol) of t-amyl alcohol were charged and reacted at 25° C. for 1 hour in a nitrogen atmosphere. After finishing the reaction, formation of t-amyl fluoride (master ion, 90) was confirmed by GC-MS measurement on the reaction mixture. The yield of the reaction was 62%.

EXAMPLE 12
Synthesis of 1,3-difluorobutane

To a reaction vessel, 7.74 g (6.48 m mol) of a 11.4 wt % solution of DFI in acetonitrile which was obtained by the same procedures as Example 1, and 0.29 g (3.24 m mol) of 1,3-butanediol were charged and reacted at 25° C. for 1 hour in a nitrogen atmosphere. After finishing the reaction, formation of 1,3-difluorobutane (master ion, 93) was confirmed by GC-MS measurement on the reaction mixture. The yield of the reaction was 61%.

EXAMPLE 13
Synthesis of difluorodiphenylmethane

To a reaction vessel, 2.43 g (17.8 m mol) of DFI obtained by the same procedures as Example 1, 1.63 g (8.9 m mol) of benzophenone and 20 ml of acetonitrile were charged and reacted at 84° C. for 28 hours in a nitrogen atmosphere. After finishing the reaction, formation of difluorodiphenyl-methane (master ion, 204, base peak 127) was confirmed by GC-MS measurement on the reaction mixture. The yield of the reaction was 45% by GC analysis.

EXAMPLE 14
Synthesis of 1,1-difluorohexane and 1-fluoro-l-cyclohexene

To a reaction vessel, 1.99 g (11.7 m mol) of DFI obtained by the same procedures as Example 1, 0.85 g (8.6 m mol) of cyclohexanone, 8.5 g of 1,2-dimethoxyethane and 0.15 g of 25% fuming sulfuric acid were charged and reacted at 20 to 25° C. for 96 hours in a nitrogen atmosphere. After finishing the reaction, formation of 1,1-difluorohexane (master ion, 120) and 1-fluoro-1-cyclohexene (master ion, 100) was confirmed by GC-MS measurement on the reaction mixture. The yield of 1-fluoro-l-cyclohexene in the reaction was 77% by GC analysis.

EXAMPLE 15
Synthesis of 4,4'-dichloro-difluoro-diphenylmethane

To a reaction vessel, 12.2 g (10.2 m mol as DFI) of a DFI solution in acetonitrile which was obtained by the same procedures as Example 1, and 1.26 g (5.04 m mol) of 4,4'-dichloro-benzophenone were charged and reacted at 84° C. for 24 hours. After finishing the reaction, formation of 4,4'-dichloro-difluorodiphenylmethane (master ion, 272) was confirmed by GC-MS measurement on the reaction mixture. The yield of 4,4'-dichloro-difluorodiphenylmethane in the reaction was 90% by GC analysis.

EXAMPLE 16
Synthesis of α,α-difluorotoluene

To a reaction vessel, 12.43 g (17.8 m mol) of DFI obtained by the same procedures as Example 1, 0.93 g (8.8 m mol) of benzaldehyde and 25 ml of acetonitrile were charged and reacted at 80 for 8 hours in a nitrogen atmosphere. After finishing the reaction, formation of α α-difluorotoluene (master ion, 128) was confirmed by GC-MS measurement on the reaction mixture. The yield in the reaction was 80% by GC analysis.

EXAMPLE 17
Synthesis of 4,4'-difluorobenzophenone

To a reaction vessel, 4.08 g (30.00 m mol) of DFI obtained by the same procedures as Example 1, 1.07 g (5.00 m mol) of 4,4'-dihydroxybenzophenone and 50 ml of acetonitrile were charged and reacted at 84° C. for 2 hours in a nitrogen atmosphere. After finishing the reaction, formation of 4,4'-difluorobenzophenone (master ion, 218, base peak 123) was confirmed by GC-MS measurement on the reaction mixture. The yield in the reaction was 20% by GC analysis.

EXAMPLE 18
Synthesis of Methallyl Fluoride

To a reaction vessel, 1.783 g (1.50 m mol) of a 11.4 wt % solution of DFI in acetonitrile which was obtained by the same procedures as Example 1, 0.108 g (1.50 m mol) of methallyl alcohol and 6 ml of acetonitrile were charged and reacted at 25° C. for 4 hours in a nitrogen atmosphere.

After finishing the reaction, formation of methallyl fluoride (master ion, 74) was confirmed by GC-MS measurement on the reaction mixture. The yield of the reaction was 95% by GC analysis.

EXAMPLE 19
Synthesis of Cyclohexyl Fluoride

To a reaction vessel, 1.783 g (1.50 m mol) of a 11.4 wt % solution of DFI in acetonitrile which was obtained by the same procedures as Example 1, 0.150 g (1.50 m mol) of cyclohexanol and 6 ml of acetonitrile were charged and reacted at 25° C. for 4 hours in a nitrogen atmosphere. After finishing the reaction, formation of cyclohexyl fluoride (master ion, 102) and cyclohexane (master ion, 82) was confirmed by GC-MS measurement on the reaction mixture. The yield of the reaction was 10% in cyclohexyl fluoride and 90% in cyclohexane, respectively by GC analysis.

EXAMPLE 20
Synthesis of isopropyl Fluoride

To a reaction vessel, 1.783 g (1.50 m mol) of a 11.4 wt % solution of DFI in acetonitrile which was obtained by the same procedures as Example 1, 0.09 g (1.50 m mol) of isopropyl alcohol and 6 ml of acetonitrile were charged and reacted at 25° C. for 4 hours in a nitrogen atmosphere. After finishing the reaction, formation of isopropyl fluoride (master ion, 62) and propylene (master ion, 42) was confirmed by GC-MS measurement on the reaction mixture. The yield of the reaction was 80% in isopropyl fluoride and 20% in propylene, respectively by GC analysis.

EXAMPLE 21
Synthesis of p-fluoronitrobenzene

To a reaction vessel, 41.6 g (40.8 m mol) of a 13.6 wt % DFI solution in acetonitrile, 2.84 g (20.4 m mol) of p-nitrophenol and 2.03 g (20.1 m mol) of triethylamine were charged and reacted at 84° C. for 15 hours in a nitrogen atmosphere. After finishing the reaction, formation of p-fluoronitrobenzene (master ion, 141) was confirmed by GC-MS measurement on the reaction mixture. The yield of the reaction was 60% by GC analysis.

EXAMPLE 22
Synthesis of p-fluoronitrobenzene

To a reaction vessel, 20. g (16.0 m mol) of a 10.7 wt % DFI solution in acetonitrile, 1.256 g (8.10 m mol) of p-nitrothiophenol were charged and reacted at 84° C. for 16 hours in a nitrogen atmosphere. After finishing the reaction, the reaction mass was poured into 20 ml of saturated aqueous sodium hydrogen carbonate solution to hydrolyze DFI, successively acidified with conc.HCl to pH 2 or less and extracted with 50 ml of dichloromethane. Formation of p-fluoronitrobenzene (master ion, 141) was confirmed by GC-MS measurement on the reaction mixture. The yield of the reaction was 20% by GC analysis.

EXAMPLE 23
Synthesis of 2,4-dinitrofluorobenzene

To a reaction vessel, 1.64 g (8.10 m mol) of 2,4-dinitrochlorobenzene, 2.21 g (16.23 m mol) of DFI, and 25 ml of acetonitrile were charged and reacted at 84° C. for 7 hours in a nitrogen atmosphere. After finishing the reaction, formation of 2,4-dinitrofluorobenzene (master ion, 186, base peak 94) was confirmed by GC-MS measurement on the reaction mixture. The yield of the reaction was 96.0% by GC analysis.

EXAMPLE 24
Synthesis of dichlorofluoronitrobenzene

To a reaction vessel, 0.74 g (2.50 m mol) of pentachloronitrobenzene, 1.77 g (13.00 m mol) of DFI, and 25 ml of acetonitrile were charged and reacted at 84° C. for 2 hours in a nitrogen atmosphere. After finishing the reaction, formation of dichlorotrifluoronitrobenzene (master ion, 245, master ion +2 247, master ion +4 249, base peak 245) was confirmed by GC-MS measurement on the reaction mixture, and the yield was 28.0% by GC analysis. Formation of trichloro-difluoronitrobenzene (master ion 261, master ion +2 263, master ion +4 265, base peak 205) was also confirmed and the yield was 11.3%. Formation of tetrachlorofluoronitrobenzene (master ion 277, master ion +2 279, master ion +4 281, master ion +6 283, base peak 221) was further confirmed and the yield was 9.0%.

EXAMPLE 25
Synthesis of Benzoyl Fluoride

To a reaction vessel, 1.41 g (10.03 m mol) of benzoyl chloride, 1.63 g (11.97 m mol) of DFI, and 25 ml of acetonitrile were charged and reacted at 84° C. for 2 hours in a nitrogen atmosphere. After finishing the reaction, formation of benzoyl fluoride (master ion, 124, base peak 124) was confirmed by GC-MS measurement on the reaction mixture. The yield of the reaction was 71.0% by GC analysis.

EXAMPLE 26
Synthesis of 2-fluoro-1,3-dimethylimidazolinium chloride (DMFC)

To a 200 ml four necked reaction flask, 30.42 g (0.1799 mol) of 2-chloro-1,3-dimethylimidazolinium chloride (DMC), 15.11 g (0.3598 mol) of sodium fluoride and 104.9 g of acetonitrile were charged and reacted at 85° C. for 8 hours in a nitrogen atmosphere. After cooling the reaction mixture to 25° C., inorganic salt was separated from the reaction mixture to obtain 116.09 g of an acetonitrile solution of DMFC (MW. 152.60). Concentration of DMFC in the solution was 21.01 wt %, and the yield was 89%.

Physical properties were as follows.

FABMS; 117[(M–Cl)$^-$], 269 [(2×M–Cl)$^+$], F-analysis: calculated 2.6 wt %, found 2.7 wt %. Cl-analysis: calculated 4.8 wt %, found 4.9 wt %. $^1$H-NMR (δ, ppm, CH$_3$CN solvent, CH$_3$CN basis, 25° C.): 2.98 (s, 6H, —CH$_3$×2), 3.91(s, 4H, —CH$_2$CH$_2$—). $^{13}$C-NMR (δ, ppm, CH$_3$CN solvent, DMSO-d$_6$ base, 25° C.): 31.3 (s, —CH$_3$×2), 46.8 (s, —CH$_2$CH$_2$—), 157.7 (d, J=280 Hz, C—F).

EXAMPLE 27
Synthesis of n-octyl Chloride

To a reaction vessel, 0.5789 g (4.445 m mol) of n-octyl alcohol, and 3.29 g of an 21.01 wt % solution of DMFC in acetonitrile (0.691 g, 4.530 m mol as DMFC) were charged and reacted at room temperature for 5 hours in a nitrogen atmosphere. After finishing the reaction, GC analysis of the reaction mixture revealed 93.1% yield of n-octyl chloride. Unreacted n-octyl alcohol was 6.6%.

COMPARATIVE EXAMPLE 4
Synthesis of n-octyl Chloride

To a reaction vessel, 0.7333 g (5.631 m mol) of n-octyl alcohol, and 0.956 g (5.655 m mol) of DMC and 3.8 g of acetonitrile were charged and reacted at room temperature for 6 hours in a nitrogen atmosphere. After finishing the reaction, GC analysis of the reaction mixture revealed 29.3% yield of n-octyl chloride. Unreacted n-octyl alcohol was 70.0%.

EXAMPLE 28
Synthesis of n-benzoyl Chloride

To a reaction vessel, 0.566 g (4.636 m mol) of benzoic acid and 3.34 g of 21.01 wt % DMFC solution in acetonitrile (0.707 g, 4.636 m mol as DMFC) were charged and reacted at room temperature for 3 hours in a nitrogen atmosphere. After finishing the reaction, GC analysis of the reaction mixture revealed that the yield of benzoyl chloride was 91.9% and the yield of benzoyl fluoride was 8.0%.

EXAMPLE 29
Synthesis of α-chloro-α-fluorotoluene

To a reaction vessel, 0.9935 g (9.361 m mol) of benzaldehyde and 6.81 g of 21.01 wt % DMFC solution in acetonitrile (1.431 g, 9.4 m mol as DMFC) were charged and reacted at 85° C. for 17 hours in a nitrogen atmosphere. After finishing the reaction, formation of α-chloro-α-fluorotoluene (master ion 144, base peak 109) and formation of benzal chloride (master ion 160, base peak 125) were confirmed by GC-MS measurement of the reaction mixture. The yield of α-chloro-α-fluorotoluene was 63.6%, the yield of benzal chloride was 19.7% and the unreacted benzaldehyde was 14.5% by GC analysis.

EXAMPLE 30
Synthesis of 2-fluoro-1,3-dimethylimidazolinium Bromide (DMFB)

To a 300 ml four necked flask, 13.78 g (0.101 mol) of 2,2-difluoro-1,3-dimethylimidazolidine(DFI), 10.25 g (0.0995 mol) of sodium bromide, and 126.5 g of acetonitrile were charged and reacted at 25° C. for 4 hours in a nitrogen atmosphere. The yield of 2-fluoro-1,3-dimethylimidazolinium=bromide was 99%.

Physical properties were as follows.

FABMS; 117[(M-Br)+], 313 [(2×M-Br)+], 315[isotope of (2× M-Br)+]. Br-analysis: calculated 10.51 wt %, found 10.42 wt %. $^1$H-NMR (δ, ppm, CH$_3$CN solvent, CH$_3$CN basis, 22° C.): 3.00 (s, 6H, —CH$_3$×2), 3.92(s, 4H, —CH$_2$CH$_2$—), $^{13}$C-NMR (δ, ppm, CH$_3$CN solvent, DMSO-d$_6$ basis, 22° C.): 31.5 (s, —CH$_3$×2), 46.8(s, —CH$_2$CH$_2$—), 157.6 (d, J=278 Hz, C—F).

EXAMPLE 31
Synthesis of n-octyl Bromide

To a reaction vessel, 0.247 g (1.9 m mol) of n-octyl alcohol, 1.60 g of a 25.91 wt % solution of DMFB in acetonitrile (0.414 g, 2.1 m mol as DMFB) and 3.86 g of acetonitrile were charged and reacted at room temperature for 5 hours in a nitrogen atmosphere. After finishing the reaction, formation of n-octyl bromide (master ion 192, base peak 135) was confirmed by GC-MS measurement of the reaction mixture. The yield of n-octyl bromide was 98.8% by GC analysis.

EXAMPLE 32
Synthesis of Benzoyl Bromide

To a reaction vessel, 0.24 g (2.0 m mol) of benzoic acid, 1.60 g of a 25.91 wt % DMFB solution in acetonitrile (0.414 g, 2.1 m mol as DMFB), and 3.86 g of acetonitrile were charged and reacted at room temperature for 43 hours in a nitrogen atmosphere. The results of the reaction by GC analysis were 11.0% in benzoyl bromide, 31.5% in benzoyl fluoride, 26.0% in benzoic anhydride, and 16.0% in unreacted benzoic acid.

EXAMPLE 33
Synthesis of 2-fluoro-1,3-dimethylimidazolinium Iodide (DMFI)

To a 300 ml four necked flask, 13.56 g (0.10 mol) of 2-fluoro-1,3-dimethylimidazolidine (DFI), 15.0 g (0.10 mol) of sodium iodide and 125 g of acetonitrile were charged and reacted at 250° C. for 4 hours in a nitrogen atmosphere under light shielding. The yield of 2-fluoro-1,3-dimethylimidazolinium=iodide (DMFI) was 95%.

Physical properties were as follows.

FABMS; 117 [(M-1)$^+$], 361 [(2×M-1)$^+$]. F analysis : calculated 2.47 wt %, found 2.77 wt %. I analysis: calculated 16.38 wt %, found 16.41 wt %. $^1$H-NMR ($\delta$, ppm, CH$_3$CN solvent, CH$_3$CN base, 24° C.): 3.02 (s, 6H, —CH$_3$×2), 3.93(s, 4H, —CH$_2$CH$_2$—). $^{13}$C-NMR ($\delta$, ppm, CH$_3$CN solvent, DMSO-d6 basis, 24° C.): 31.6 (s, —CH$_3$×2), 46.7(s, —CH$_2$CH$_2$—), 157.6 (d, J=278 Hz, C—F).

EXAMPLE 34
Synthesis of Benzyl Iodide

To a reaction vessel, 0.216 g (2.0 m mol) of benzyl alcohol, 1.92 g of a 31.73 wt % DMFI solution in acetonitrile (0.610 g, 2.5 m mol as DMFI) and 3.8 g of acetonitrile were charged and reacted at room temperature for 5 hours in a nitrogen atmosphere under light shielding. After finishing the reaction, formation of benzyl iodide (master ion 218, base peak 92) was confirmed by GC-MS measurement of the reaction mixture. The yield of benzyl iodide was 92.2% by GC analysis.

EXAMPLE 35
Synthesis of Benzoyl Fluoride

To a reaction vessel, 0.60 g (4.91 m mol) of benzoic acid, 4.13 g of a 31.73 wt % DMFI solution in acetonitrile (1.31 g, 5.36 m mol as DMFI) and 3.8 g of acetonitrile were charged and reacted at room temperature for 12 hours in a nitrogen atmosphere under light shielding. Reaction result by GC analysis were 35.7% in benzoyl fluoride, 17.2% in benzoic anhydride and 40.6% in unreacted benzoic acid.

EXAMPLE 36
Synthesis of 2-iodo-1,3-dimethylimidazolinium=iodide

To a 100 ml four necked flask, 8.45 g (0.05 mol) of 2-chloro-1,3-dimethylimidazolinium=chloride, 29.98 g (0.20 mol) of sodium iodide, and 60 ml of acetonitrile were charged and reacted at 25° C. for 55 hours in a nitrogen atmosphere under light shielding. After finishing the reaction, 500 ml of dry acetone was added to a slurry like reaction mass, excess sodium iodide and unreacted 2-chloro-1,3-dimethylimidazolinium=chloride were extracted into the organic solvent layer, and the reaction mass was filtered to obtain crude crystals of the desired product as a filter cake. The crude crystals of 2-iodo-1,3-dimethylimidazolinium=iodide has purity of 63.58% and contained sodium chloride.

Physical properties were as follows.

I-analysis : calculated 45.84%, found 44.9%. $^1$H-NMR ($\delta$, ppm, D$_2$O/CD$_3$CN=2/1, TMS basis,): 3.19 (s, 6H, —CH$_3$× 2), 3.97(s, 4H, —CH$_2$CH$_2$—). $^{13}$C-NMR ($\delta$, ppm, D$_2$O/ CD$_3$CN=2/1, CD$_3$CN basis): 37.7 (s, —CH$_3$×2), 50.6 (—CH$_2$CH$_2$—), 134.9 (C—I).

EXAMPLE 37
Synthesis of 2-fluoro-1,3-dimethylimidazolinium=iodide

To a 100 ml four necked flask, 19.78 g (0.017 mol) of a 11.7 wt % DFI solution in acetonitrile, 2.55 g (0.017 mol) of sodium iodide, and 10 ml of acetonitrile were charged and reacted at 25° C. for 3 hours in a nitrogen atmosphere under light shielding. 2-Fluoro-1,3-dimethylimidazolinium=iodide was thus prepared.

EXAMPLE 38
Synthesis of Benzyl Iodide

To a 100 ml four necked flask, 8.45 g (0.05 mol) of 2-chloro-1,3-dimethylimidazolinium=chloride, 29.98 g (0.20 mol) of sodium iodide and 60 ml of acetonitrile were charged and reacted at 25° C. for 55 hours in a nitrogen atmosphere under light shielding. Successively, 5.4 g (0.05 mol) of benzyl alcohol was added to the reaction mass and reacted at 60° C. for 24 hours in a nitrogen atmosphere under light shielding. After finishing the reaction, formation of benzyl iodide (master ion, 218) was confirmed by GC-MS measurement of the reaction mixture. The yield of the reaction was 62%.

EXAMPLE 39
Synthesis of Benzyl Iodide

To 2-fluoro-1,3-dimethylimidazolinium=iodide which was obtained in Example 33, 1.2 g (0.011 mol) of benzyl alcohol was added and reacted at 25° C. for 24 hours in a nitrogen atmosphere under light shielding. After finishing the reaction, formation of benzyl iodide (master ion 218) was confirmed by GC-MS measurement. The yield in the reaction was 90%.

EXAMPLE 40
Synthesis of 1,3-dimethyl-2-chloro-imidazolinium =iodide (DMCI)

To a 100 ml four necked reaction flask, 16.90 g (0.10 mol) of 2-chloro-1,3-dimethylimidazolinium=chloride, 14.99 g (0.100 mol) of sodium iodide and 60 g of acetonitrile were charged and reacted at room temperature for 40 hours in a nitrogen atmosphere under light shielding. The inorganic salt was filtered off from the reaction mixture to obtain 82.6 g a DMCI/actonitrile solution having a concentration of 27.3%. The yield of DMCI was 86.6%.

The concentration of DMCI was determined by reacting DMCI with aniline and measuring the resultant derivative with high performance liquid chromatography. Concentration of chlorine ion and iodine ion was measured with a silver nitrate titration method. The scanning range of GC-MS was 500≧M/Z≧50.

Properties were as follows.

Iodine content of the above solution: calculated 13.3%, found 13.1%. Chlorine content of the above solution: calculated 3.7%, found 3.8%. $^1$H-NMR ($\delta$, ppm, CH$_3$CN solvent, CH$_3$CN basis, 21° C.): 3.12 (s, 6H, —CH$_3$×2), 4.00 (s, 4H, —CH$_2$CH$_2$—). $^{13}$C-NMR ($\delta$, ppm, CH$_3$CN solvent, DMSO-d$_6$ base, 21): 34.5 (s, —CH$_3$×2), 49.9(s, —CH$_2$CH$_2$—), 155.9 (s, =C—Cl). FAB-MS (matrix: m-nitrobenzyl alcohol): [(DMCI-I)+], 393 [(2×DMCI-I)+].

EXAMPLE 41
Synthesis of Benzyl Iodide

To a reaction vessel, 1.08 g (9.98 m mol) of benzyl alcohol, and 11.43 g of 27.3 wt % DMCI solution in acetonitrile (3.12 g, 11.98 m mol as DMCI) were charged and reacted at 60° C. for 40 hours in a nitrogen atmosphere under light shielding. After finishing the reaction, formation of benzyl iodide (master ion 218, base peak 92) was confirmed by GC-MS measurement of the reaction mixture. The yield of benzyl iodide was 86.5% by GC analysis.

EXAMPLE 42
Synthesis of Benzoyl Chloride

To a reaction vessel, 1.22 g (9.99 m mol) of benzoic acid, 11.43 g of a 27.3 wt % DMCI solution in acetonitrile (3.12 g, 11.98 m mol as DMCI), and 20.0 g of acetonitrile were charged and reacted at 60° C. for 24 hours in a nitrogen atmosphere under light shielding. After finishing the reaction, formation of benzoyl chloride (master ion 140, base peak 105) was confirmed by GC-MS measurement and GC analysis of the reaction mixture.

Benzoic anhydride (base peak 105) was formed as a by-product. The yield in the reaction is individual 92.5% in benzoyl chloride and 5.5% in benzoic anhydride.

EXAMPLE 43
Synthesis of 1,3-dimethyl-2-chloro-imidazolinium= Bromide (DMCB)

To a 500 ml four necked reaction flask, 50.00 g (0.296 mol) of 2-chloro-1,3-dimethylimidazolinium=chloride, 30.86 g (0.300 mol) of sodium bromide and 240 ml of acetonitrile were charged and reacted at 80° C. for 30 hours in a nitrogen atmosphere. The reaction mixture was hot filtered at 70° C. or more to remove inorganic salt. The solvent was eliminated from the filtrate to obtain a solid. Recrystallization was carried out by using 0.7 ml of acetonitrile for 1 g of the precipitated solid. DMCB thus obtained was 37.5 g as white crystal. The yield was 59.34%.

Physical properties were as follows.

Bromine analysis: calculated 37.4%, found 37.7%. Chlorine analysis: calculated 16.6%, found 16.4%. $^1$H-NMR ($\delta$, ppm, $CD_3CN$ solvent, TMS basis, 21° C.): 3.15 (s, 6H, —$CH_3\times 2$), 4.00(s, 4H, —$CH_2CH_2$—). $^{13}$C-NMR ($\delta$, ppm, $CD_3CN$ solvent, $CD_3CN$-$d_6$ basis, 21 ): 35.2 (s, —$CH_3\times 2$), 50.8(s, —$CH_2CH_2$—), 156.3 (s, =C—Cl). FABMS (matrix :m-nitrobenzyl alcohol): 133[(DMCB–Br)+], 347[(2× DMCB–Br)+peak of isotope].

EXAMPLE 44
Synthesis of n-octyl Bromide

To a reaction vessel, 1.30 g (9.98 m mol) of n-octyl alcohol, 2.14 g (10.02 m mol) of DMCB and 50 ml of acetonitrile were charged and reacted at 84° C. for 33 hours. After finishing the reaction, formation of n-octyl bromide (base peak 55, coincidence with a standard chart) was confirmed by GC-MS measurement of the reaction mixture. The yield in the reaction was 96% by GC analysis.

EXAMPLE 45
Synthesis of Benzyl Bromide

To a reaction vessel, 1.08 g (9.99 m mol) of benzyl alcohol, 2.14 g (10.02 m mol) of DMCB and 50 ml of acetonitrile were charged and reacted at 84° C. for 24 hours in a nitrogen atmosphere. After finishing the reaction, formation of benzyl bromide (master ion 170, base peak 91) was confirmed by GC-MS measurement of the reaction mixture. The yield in the reaction was 85% by GC analysis.

EXAMPLE 46
Synthesis of Benzoyl Chloride

To a reaction vessel, 1.22 g (9.99 m mol) of benzoic acid, 2.14 g (10.02 m mol) of DMCB and 50 ml of acetonitrile were charged and reacted at 84° C. for 24 hours. After finishing the reaction, formation of benzoyl chloride (master ion 140, base peak 105) and benzoic anhydride (master peak 105) was confirmed by GC-MS measurement of the reaction mixture and by comparison of retention time with a reference material of GC. The yield in the reaction was 66% and 12%, respectively.

EXAMPLE 47
Synthesis of 3,3'-difluoro-2-methylpropene

To a 300 ml autoclave, 1.70 g (24.3 m mol) of methacrolein, 55 g of acetonitrile, 6.61 g (48.6 m mol) of DFI and 10 g (99 m mol) of triethylamine were charged, closed up tightly after substituting the reaction system with nitrogen, and reacted at 100° C. for 5 hours. The internal pressure was increased up to 1.96×105 Pa in the course of the reaction. After cooling, a small amount of water was added to the reaction mass and GC and GC-MS measurements were successively carried out. As a result, formation of 3,3-difluoro-2-methylpropene (master ion 91) in the yield of 90% and 10% of unreacted methacrolein (master ion 70) were confirmed.

EXAMPLE 48
Synthesis of 3,3'-difluoro-propene

To a 300 ml autoclave, 1.40 g (25 m mol) of acrolein, 55 g of acetonitrile and 6.61 g (48.6 m mol) of DFI, and 10 g (99 m mol) were charged, closed up tightly after substituting the reaction system with nitrogen, and reacted at 100° C. for 5 hours. The internal pressure was increased up to 1.96 ×105 Pa in the course of the reaction. After cooling, a small amount of water was added to the reaction mass and successively GC and GC-MS measurements were carried out. As a result, formation of 3,3-difluoro-propene (master ion 78) in the yield of 88% and 12% of unreacted methacrolein (master ion 56) were confirmed.

EXAMPLE 49
Sythesis of 3,3'-difluoro-propene

To a reaction vessel, 5 g (4.40 m mol) of a 11 wt % DFI solution in acetonitrile, and 0.255 g (4.40 m mol) of allyl alcohol were charged and reacted at 25° C. for 4 hours in a nitrogen atmosphere. After finishing the reaction, formation of 3-fluoropropene (master ion 60) was confirmed by GC-MS measurement of the reaction mixture. The yield in the reaction was 98% by GC measurement.

EXAMPLE 50
Synthesis of 2-fluoroethylmethacrylate

To a reaction vessel, 8 g (6.48 m mol) of a 9.25% DFI solution in acetonitrile, and 0.842 g (6.48 m mol) of 2-hydroxyethylmethacrylate were charged and reacted at 25° C. for 2 hours. After finishing the reaction, formation of 2-fluoroethylmethacrylate (master ion 132) was confirmed by GC-MS measurement of the reaction mixture. The yield in the reaction was 94% by GC analysis.

What is claimed is:

1. A preparation process of a fluorine compound represented by the formula (9-1):

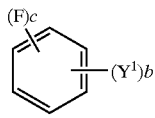
(9)

wherein $Y^1$ is an electrophilic substituent, b is an integer of 1 to 5, c is an integer of 1 to 5, and b+c<6, comprising reacting a compound of phenol or thiophenol represented by the formula (9)

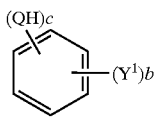
(9)

wherein Q is an oxygen or a sulfur atom, and $Y^1$, b and c are the same as in the formula (9-1), with the fluorinating agent represented by the formula (1):

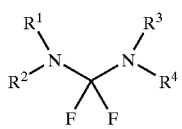
(1)

wherein $R^1$ to $R^4$ is substituted, saturated or unsaturated alkyl group, saturated or unsaturated aryl group, and are the same or different; $R^1$ and $R^2$ or $R^3$ and $R^4$ are individual groups or are bonded to form a ring including a nitrogen atom; or $R^1$ and $R^3$ are individual groups or are bonded to form a ring including a nitrogen atom.

2. A preparation process of a fluorine compound represented by the formula (10-1):

$R^{12}$—CHF$_2$ (10-1)

wherein $R^{12}$ is a substituted or unsubstituted, saturated or unsaturated alkyl group, or a substituted or unsubstituted aryl group, comprising reacting an aldehyde compound represented by the formula (10):

$R^{12}$—CHO (10)

wherein $R^{12}$ as in the formula (10-1), with the flurinating agent represented by the formula (1):

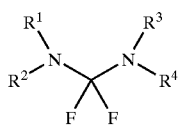
(1)

wherein $R^1$ to $R^4$ substituted, saturated or unsaturated alkyl group, saturated or unsaturated aryl group, and are the same or different; $R^1$ and $R^2$ or $R^3$ and $R^4$ are individual groups or are bonded to form a ring including a nitrogen atom; or $R^1$ and $R^3$ are individual groups or are bonded to form a ring including a nitrogen atom.

3. A preparation process of a flurine compound represented by the formula (11-1):

(11-1)

wherein $R^{13}$ and $R^{14}$ are substituted or unsubstituted, saturated or unsaturated alkyl group or a substituted or unsubstituted aryl group and are the same or different; and $R^{13}$ and $R^{14}$ are individual groups or are bonded to form a ring, comprising reacting a ketone compound represented by the formula (11)

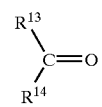
(11)

wherein $R^{13}$ and $R^{14}$ are the same as in the formula (11-1), with the fluorinating agent represented by the formula (1):

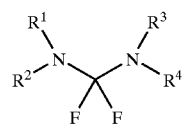
(1)

wherein $R^1$ to $R^4$ is substituted or unsubstituted, saturated or unsaturated alkyl group, saturated or unsaturated aryl group, and are the same or different; $R^1$ and $R^2$ or $R^3$ and $R^4$ are individual groups or are bonded to form a ring including a nitrogen atom; or $R^1$ and $R^3$ are individual groups or are bonded to form a ring including a nitrogen atom.

4. A preparation process of an acid fluoride represented by the formula (12-1):

$R^{15}$—COF (12-1)

wherein $R^{15}$ is a substituted or unsubstituted, saturated or unsaturated alkyl group or a substituted or unsubstituted aryl group, comprising reacting a carboxyl compound represented by the formula (12):

$R^{15}$—COOH (1)

wherein $R^{15}$ is the same as in the formula (12-1), with the fluorinating agent represented by the formula (1):

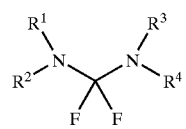
(1)

wherein $R^1$ to $R^4$ is substituted or unsubstituted, saturated or unsaturated alkyl group, saturated or unsaturated aryl group, and are the same or different; $R^1$ and $R^2$ or $R^3$ and $R^4$ are individual groups or are bonded to form a ring including a nitrogen atom; or $R^1$ and $R^3$ are individual groups or are bonded to form a ring including a nitrogen atom.

5. A preparation process of a fluorine compound represented by the formula (13-1):

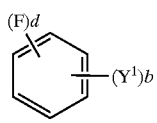

wherein $Y^1$ is an electrophilic substituent, b and d are integers of 1 to 5, and $b+d \leq 6$, comprising reacting an aromatic compound represented by the formula (13):

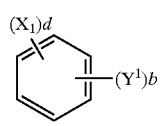

wherein $X^1$ is a halogen atom except fluorine, and $Y^1$, b and d are the same as in the formula (13-1), with the fluorinating agent represented by the formula (1)

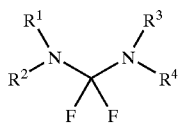

wherein $R^1$ to $R^4$ is substituted or unsubstituted, saturated or unsaturated alkyl group, saturated or unsaturated aryl group, and are the same or different; $R^1$ and $R^2$ or $R^3$ and $R^4$ are individual groups or are bonded to form a ring including a nitrogen atom; or $R^1$ and $R^3$ are individual groups or are bonded to form a ring including a nitrogen atom.

6. A preparation process of a fluorine containing olefinic compound represented by the formula (25)

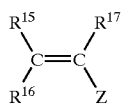

wherein $R^{15}$ to $R^{17}$ are a hydrogen atom or a lower alkyl group having 1 to 3 carbon atoms and are the same or different; and Z is —(Y)n—$CHF_2$, —(Y)n—$CH_2F$ or —CO—O—(Y)n—$CH_2F$, wherein Y is —$CH_2$— and n is 0 or an integer of 1 to 5, comprising reacting the fluorinating agent represented by the formula (1);

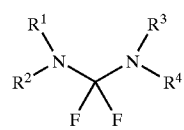

wherein $R^1$ to $R^4$ is a substituted or unsubstituted, saturated or unsaturated alkyl group, saturated or unsaturated aryl group, and are the same or different; $R^1$ and $R^2$ or $R^3$ and $R^4$ individual groups or are bonded to form a ring including a nitrogen atom; or $R^1$ and $R^3$ are individual groups or are bond to form a ring including a nitrogen atom, with an olefinic compounds represented by the formula (24)

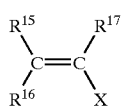

wherein $R^{15}$ to $R^{17}$ are hydrogen atom or a lower alkyl group having 1 to 3 carbon atoms and are the same or different; and X is —(Y)n—CHO—, —(Y)n—$CH_2OH$, or —CO—O—(Y)n—$CH_2OH$, wherein Y is —$CH_2$— and n is 0 or an integer of 1 to 5.

* * * * *

UNITED STATES PATENT AND TRADEMARK OFFICE
CERTIFICATE OF CORRECTION

PATENT NO. : 6,458,990 B1  
DATED : October 1, 2002  
INVENTOR(S) : Hiroshi Sonoda et al.

It is certified that error appears in the above-identified patent and that said Letters Patent is hereby corrected as shown below:

Column 45,  
Line 5, change "(9)" to -- (9-1) --;  
Line 12, change "b + c <6" to -- b + c$\leq$6 --;  
Line 34, after "substituted" insert -- or unsubstituted --;  
Line 50, after "$R^{12}$" insert -- is the same --; change "flurinating" to -- fluorinating --;  
Line 60, after "$R^4$" insert -- is --; after "substituted" insert -- or unsubstituted --.

Column 48,  
Lines 11-12, change "-$CH_2$-" to -- -$CH_2$- --; change "$_{\text{and n is O or an integer of}}$" to -- and n is 0 or an integer of --;  
Line 26, change "bond" to -- bonded --.

Signed and Sealed this

Thirteenth Day of May, 2003

JAMES E. ROGAN  
*Director of the United States Patent and Trademark Office*